US010209209B2

(12) United States Patent
Ikeda et al.

(10) Patent No.: US 10,209,209 B2
(45) Date of Patent: Feb. 19, 2019

(54) INTERNAL TEMPERATURE MEASURING DEVICE, WRIST MOUNTING-TYPE DEVICE, AND METHOD OF MEASURING INTERNAL TEMPERATURE

(71) Applicant: SEIKO EPSON CORPORATION, Tokyo (JP)

(72) Inventors: Akira Ikeda, Chino (JP); Sakiko Shimizu, Matsumoto (JP); Kazuhiro Nishida, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 272 days.

(21) Appl. No.: 15/388,766

(22) Filed: Dec. 22, 2016

(65) Prior Publication Data
US 2017/0184523 A1  Jun. 29, 2017

(30) Foreign Application Priority Data

Dec. 28, 2015 (JP) ................................ 2015-256971

(51) Int. Cl.
| | |
|---|---|
| G01K 7/00 | (2006.01) |
| G01K 1/00 | (2006.01) |
| G01N 25/00 | (2006.01) |
| G01K 17/00 | (2006.01) |
| G01K 13/00 | (2006.01) |

(Continued)

(52) U.S. Cl.
CPC ........... *G01N 25/20* (2013.01); *A61B 5/0008* (2013.01); *A61B 5/6801* (2013.01); *A61B 5/6824* (2013.01); *G01K 7/427* (2013.01); *G01K 13/002* (2013.01)

(58) Field of Classification Search
USPC ............ 374/43, 208, 29, 142, 166, 110, 163
See application file for complete search history.

(56) References Cited

U.S. PATENT DOCUMENTS

| | | | | |
|---|---|---|---|---|
| 5,940,784 A | * | 8/1999 | El-Husayni | ............ G01N 25/18 374/43 |
| 2003/0199783 A1 | | 10/2003 | Bloom et al. | |

(Continued)

FOREIGN PATENT DOCUMENTS

| | | |
|---|---|---|
| EP | 3061389 A1 | 8/2016 |
| JP | 2002-202205 A | 7/2002 |

(Continued)

OTHER PUBLICATIONS

Pennes, Harry H., Analysis of Tissue and Arterial Blood Temperatures in the Resting Human Forearm. Journal of Applied Physiology, vol. 1, p. 93-112, Aug. 1948.

(Continued)

*Primary Examiner* — Mirellys Jagan
(74) *Attorney, Agent, or Firm* — Oliff PLC

(57) ABSTRACT

An internal temperature measuring device is configured to include an acquisition unit that acquires a one side temperature and a one side heat flux of a measurement target on a one side surface side and an opposite side temperature and an opposite side heat flux of the measurement target on an opposite side surface side; and a computation unit that computes an internal temperature of the measurement target by applying the one side temperature, the one side heat flux, the opposite side temperature, and the opposite side heat flux.

25 Claims, 18 Drawing Sheets

(51) Int. Cl.
*G01N 25/20* (2006.01)
*A61B 5/00* (2006.01)
*G01K 7/42* (2006.01)

(56) References Cited

U.S. PATENT DOCUMENTS

| | | | |
|---|---|---|---|
| 2004/0039254 A1 | 2/2004 | Stivoric et al. | |
| 2013/0223473 A1* | 8/2013 | Kim | G01K 17/00 374/29 |
| 2015/0157220 A1* | 6/2015 | Fish | A61B 5/02055 600/301 |
| 2015/0160048 A1 | 6/2015 | Schuessler | |
| 2015/0342525 A1* | 12/2015 | Justice | A61B 5/6831 600/479 |
| 2016/0066839 A1 | 3/2016 | Ikeda et al. | |
| 2016/0128631 A1* | 5/2016 | Ikeda | A61B 5/4866 600/307 |
| 2016/0252407 A1* | 9/2016 | Ikeda | G01K 13/002 374/29 |
| 2018/0039749 A1* | 2/2018 | Ikeda | G16H 40/63 |
| 2018/0113911 A1* | 4/2018 | Ikeda | G16H 40/63 |

FOREIGN PATENT DOCUMENTS

| | | |
|---|---|---|
| JP | 2008-168054 A | 7/2008 |
| JP | 2011072637 A | 4/2011 |
| JP | 2011-120917 A | 6/2011 |
| JP | 2014052350 A | 3/2014 |
| JP | 2015112488 A | 6/2015 |
| JP | 2016-057198 A | 4/2016 |
| KR | 2011-0054567 A | 5/2011 |
| WO | 2015-184206 A1 | 12/2015 |

OTHER PUBLICATIONS

May 23, 2017 European Seach Report issued in European Patent Office Application No. 16206655.9.

* cited by examiner

| SKIN TEMPERATURE $\theta_a$ OR $\theta_b$ [°C] | BLOOD FLOW PER UNIT VOLUME : $W_b$ [$m^3/(m_3 \cdot s)$] |
|---|---|
| 18.5 | 0.0000 |
| 19.1 | 0.0000 |
| 20.3 | 0.0001 |
| 21.6 | 0.0001 |
| 24.2 | 0.0002 |
| 27.4 | 0.0004 |
| 30.3 | 0.0005 |
| 32.1 | 0.0008 |
| 33.3 | 0.0012 |
| 34.1 | 0.0016 |
| 34.8 | 0.0020 |
| 35.1 | 0.0024 |
| 35.5 | 0.0029 |
| 35.8 | 0.0033 |

FIG.15

INTERNAL TEMPERATURE MEASURING DEVICE, WRIST MOUNTING-TYPE DEVICE, AND METHOD OF MEASURING INTERNAL TEMPERATURE

CROSS-REFERENCE TO RELATED APPLICATIONS

The present application claims priority to Japanese Patent Application JP 2015-256971, filed Dec. 28, 2015, the entire disclosure of which is hereby incorporated by reference herein.

BACKGROUND

1. Technical Field

Various embodiments of the present invention relate to an internal temperature measuring device and the like.

2. Related Art

An internal body temperature and base metabolism are bio-information related to a person. The internal body temperature denotes a temperature of a place deeper (inside) than the skin surface of the human body, regardless of the site of the human body.

As technologies of measuring an internal body temperature, for example, a technology in which a probe internally housing a heater is mounted on the surface of a living body, heat is applied from the heater, and the internal temperature is computed by measuring the temperature when the heat flow radiated from a living body becomes "0" (for example, refer to JP-A-2002-202205), a technology in which an internal temperature is measured by substituting heat conduction inside a living body by an equivalent circuit, that is, an electric circuit (for example, refer to JP-A-2014-052350), and the like are known. Moreover, an instrument of measuring an internal body temperature by inserting a device into the external auditory meatus is known (for example, refer to JP-A-2011-072637).

As a technology of measuring base metabolism, a technology in which an instrument equipped with a heat flow thermistor for measuring a heat flux, and a plurality of temperature sensors is attached to an arm or the like of a measurement target person, and the base metabolism is obtained based on the heat flux and the temperature difference is known (for example, refer to JP-A-2011-120917).

In order to continuously and precisely measure bio-information of a person, particularly bio-information related to a temperature such as an internal body temperature and base metabolism for a long time (for example, one day or longer), it is important to find a way to minimize the influence of various types of errors.

From the view of convenience and comfort of measurement, in an instrument having the form disclosed in JP-A-2011-072637, a device has to be inserted into the external auditory meatus and to be kept therein, and it is difficult to mention that the device is preferable. An instrument having the form disclosed in JP-A-2011-120917 may be preferable.

However, in the technology disclosed in JP-A-2011-120917, the influence of an error caused due to the shape of a measurement target site and an error caused due to biasing of a heat source position inside a living body is not taken into consideration. In other words, generally, in an arm and the like of a living body, the position of the heat source is often biased from the center. For example, in a wrist, a surface temperature and a heat flow are characterized to vary due to the difference of the position of a site between the front and the back, that is, the back side and the palm side. In JP-A-2011-120917, since measurement errors caused due to the difference of the position of a measurement site between the front and the back are not compensated for, the measurement errors caused due to the difference of the position of the measurement site between the front and the back are included.

On the other hand, in a case where the technology of JP-A-2002-202205 is applied to an instrument having the form of JP-A-2011-120917, since the technology of JP-A-2002-202205 requires a heater, it is difficult to realize an instrument having a favorably convenient and comfort size. Since a heater is required, there are disadvantages such as whether to continue driving the heater, whether to intermittently drive the heater, and how to ensure a power source during measurement taken for a long period of time.

Moreover, in a case where the technology of JP-A-2014-052350 requiring no heater is applied, the influence of an error caused due to biasing of the heat source position inside a living body is included. In other words, actually, the inside of a living body is naturally a heat conductive system including heat generation caused due to metabolism of tissue and a heat inflow from blood to the tissue, and the heat flow varies depending on the depth inside the living body.

The above-described disadvantages are not limited to measuring an internal temperature of a person and are similarly applied to measuring an internal temperature of a different animal. The same circumstances are applied to analyzing an internal temperature of a semiconductor chip such as large scale integration (LSI), and analyzing an internal temperature of a machine component or a structure body internally having a heat source.

SUMMARY

An advantage of some aspects of the invention is to provide a new technology of measuring an internal temperature which is less affected by an error.

A first aspect of the invention is directed to an internal temperature measuring device including an acquisition unit that acquires a one side temperature and a one side heat flux of a measurement target on a one side surface side and an opposite side temperature and an opposite side heat flux of the measurement target on an opposite side surface side; and a computation unit that computes an internal temperature of the measurement target by applying the one side temperature, the one side heat flux, the opposite side temperature, and the opposite side heat flux.

A second aspect of the invention is directed to the internal temperature measuring device according to the first aspect, which further includes a measurement unit that has a one side sensor section which measures the one side temperature and the one side heat flux and is provided on the one side surface side of the measurement target, and an opposite side sensor section which measures the opposite side temperature and the opposite side heat flux and is provided on the opposite side surface side of the measurement target, and in which the acquisition unit acquires a measurement result by means of the one side sensor section and the opposite side sensor section.

According to the first aspect or the second aspect of the invention, measurement requires no heater. Thus, it is possible to ensure convenience and comfort of measurement. Moreover, distribution tendency of the internal temperature of the measurement target is postulated, and the internal temperature is computed based on the surface temperature and the heat flux measured on the one side and the surface temperature and the heat flux measured on the opposite side.

Thus, it is possible to minimally restrain the influences of an error caused due to the shape of the measurement target and an error caused due to biasing of a heat source position inside the measurement target.

A third aspect of the invention is directed to the internal temperature measuring device according to the second aspect, in which the one side sensor section includes a plurality of temperature sensors, the opposite side sensor section includes a plurality of temperature sensors, and the acquisition unit acquires a one side heat flow from a plurality of temperatures measured with the one side sensor section and acquires an opposite side heat flow from a plurality of temperatures measured with the opposite side sensor section.

According to the third aspect of the invention, without providing a sensor measuring a heat flux, the heat flux can be obtained from the measurement result of the plurality of temperature sensors. Thus, it is possible to achieve simplification of the structure and reduction of the manufacturing cost.

A fourth aspect of the invention is directed to the internal temperature measuring device according to the second aspect or the third aspect, in which the measurement unit includes a first pair of sensor sections which are provided so as to interpose a first internal position of the measurement target, and a second pair of sensor sections which are provided so as to interpose a second internal position of the measurement target, and the computation unit estimates a first internal temperature by applying a measurement result obtained by means of the first pair of sensor sections, estimates a second internal temperature by applying a measurement result obtained by means of the second pair of sensor sections, and determines a final internal temperature by applying the first internal temperature and the second internal temperature.

According to the fourth aspect of the invention, for example, heat source positions inside the measurement target are set as the internal positions, and the pairs of sensor sections respectively corresponding to the internal positions are provided. Thus, it is possible to more precisely measure the internal temperature.

A fifth aspect of the invention is directed to the internal temperature measuring device according to any one of the first aspect to the third aspect, which further includes a measurement unit that has N (N≥3) sensor sections which are circumferentially disposed so as to surround the surface of the measurement target and measure a temperature and a heat flux, in which the acquisition unit selects a plurality of pairs of sensor sections in each pair of which a sensor section on the one side surface side and a sensor section on the opposite side surface side are combined together from the N sensor sections, and acquire a measurement result by means of each of the pairs of sensor sections, and the computation unit estimates a candidate of the internal temperature for each pair of sensor sections by applying the measurement result of the pair of sensor sections obtained by means of the acquisition unit, and causes a candidate satisfying a predetermined condition to be determined as a final internal temperature from the candidates.

According to the fifth aspect of the invention, it is possible to more accurately measure the internal temperature.

A sixth aspect of the invention is directed to the internal temperature measuring device according to any one of the first aspect to the third aspect, which further includes a sensor section that measures a temperature and a heat flux and is changeably disposed between the one side surface side and the opposite side surface side, in which the acquisition unit acquires a measurement result obtained when the sensor section is disposed on the one side surface side as the one side temperature and the one side heat flux, and acquires a measurement result obtained when the sensor section is disposed on the opposite side surface side as the opposite side temperature and the opposite side heat flux.

According to the sixth aspect of the invention, the temperatures and the heat fluxes on the one side surface side and the opposite side surface side can be measured with one sensor section. Thus, it is possible to achieve simplification of the structure and reduction of the manufacturing cost.

A seventh aspect of the invention is directed to the internal temperature measuring device according to any one of the first aspect to the sixth aspect, in which the computation unit computes the internal temperature of the measurement target by applying a predetermined temperature distribution indicating temperatures inside the measurement target.

According to the seventh aspect of the invention, it is possible to more accurately measure the internal temperature.

As an eighth aspect of the invention, the internal temperature measuring device according to anyone of the first aspect to the seventh aspect may be configured such that the temperature distribution is expressed through an Nth order function (N≥2) in which the internal temperature of the measurement target is a temperature peak.

As a ninth aspect of the invention, utilizing the internal temperature measurement, the internal temperature measuring device according to any one of the first aspect to the eighth aspect may be configured such that the measurement target is four limbs of a human body, and the computation unit also computes base metabolism by applying the one side heat flux and the opposite side heat flux.

The device is not limited to one body, and as a tenth aspect of the invention, the internal temperature measuring device according to any one of the second aspect to the ninth aspect may be configured such that the measurement target is four limbs of a human body, the measurement unit is internally housed in each of annular mounting instruments which are mounted on the four limbs, the acquisition unit and the computation unit are internally housed in a main body device, and each of the mounting instruments and the main body device are configured to be connected so as to perform communication therebetween.

An eleventh aspect of the invention is directed to a wrist mounting-type device including the internal temperature measuring device according to any one of the first aspect to the tenth aspect of the invention and in which a measurement target is a wrist of a human body and which has an annular shape and is mounted on the wrist.

According to the eleventh aspect of the invention, it is possible to further improve convenience and comfort of measurement.

A twelfth aspect of the invention is directed to a method of measuring an internal temperature of a measurement target through computation processing executed by a computer. The method includes acquiring a one side temperature and a one side heat flux of the measurement target on a one side surface side, and an opposite side temperature and an opposite side heat flux of the measurement target on an opposite side surface side; and computing the internal temperature of the measurement target by applying the one side temperature, the one side heat flux, the opposite side temperature, and the opposite side heat flux.

According to the twelfth aspect of the invention, it is possible to realize a method of measuring an internal temperature and obtaining an effect similar to that of the first aspect of the invention.

BRIEF DESCRIPTION OF THE DRAWINGS

Various embodiments of the invention will be described with reference to the accompanying drawings, wherein like numbers reference like elements.

FIG. 15 is an example of a correspondence table of skin temperatures and blood flow rates.

DESCRIPTION OF EXEMPLARY EMBODIMENTS

First Embodiment

As an example of an internal temperature measuring device to which various embodiments of the invention are applied, an internal temperature measuring device measuring an internal body temperature of a human body will be described.

1: Configuration of Hardware

Figure 1:
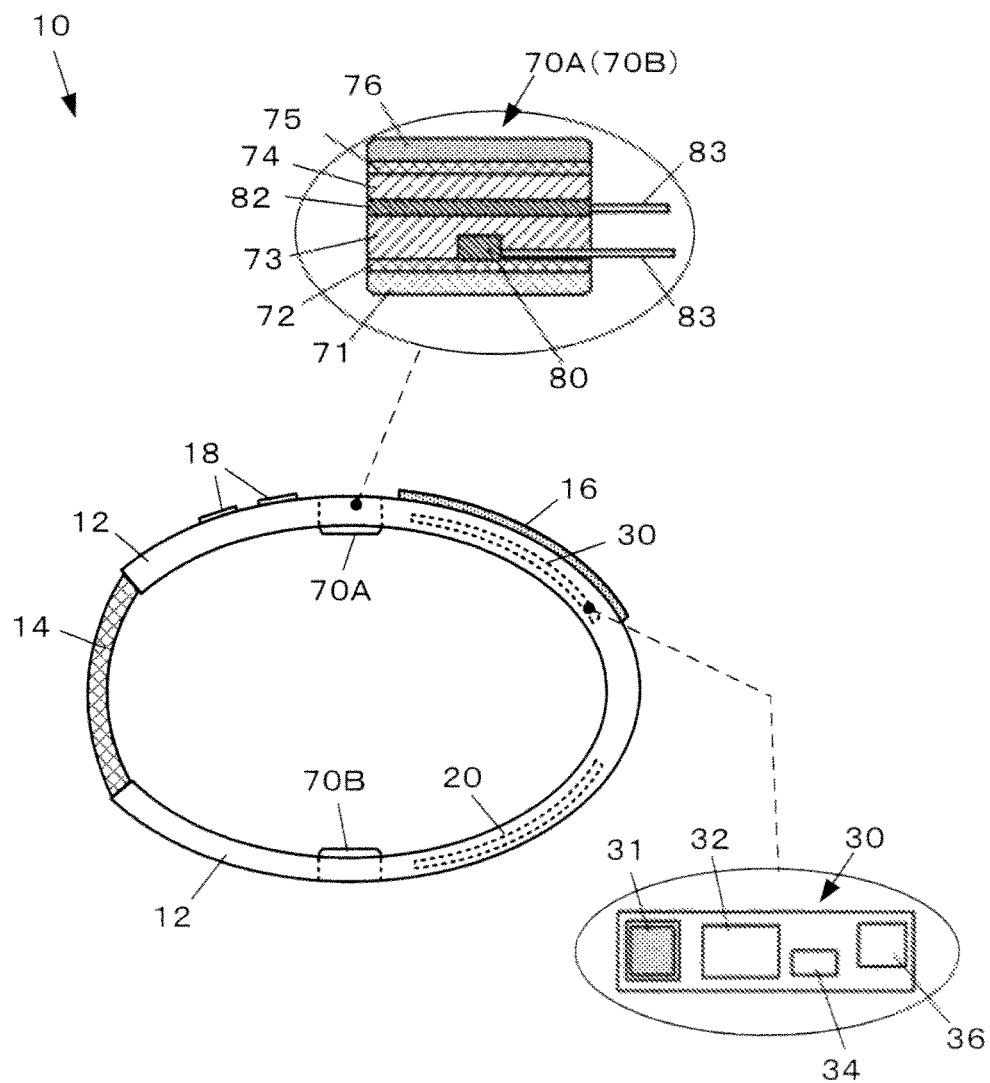
FIG. 1 is a front view illustrating a configuration example of an internal temperature measuring device of a first embodiment.
Figure 2:
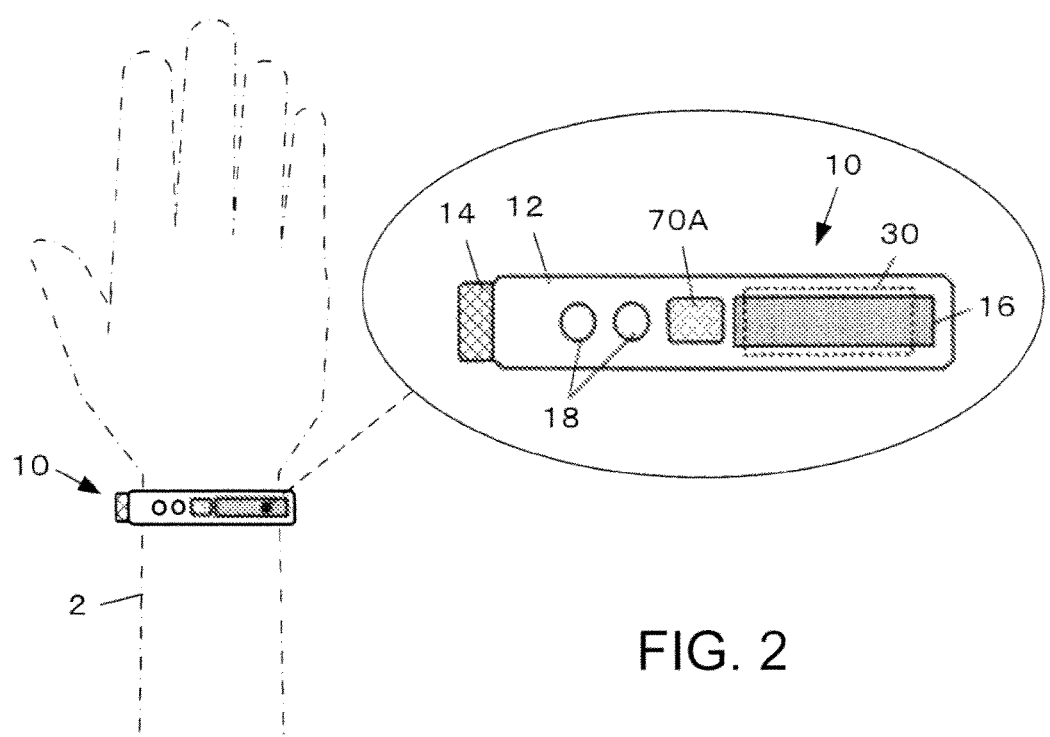
FIG. 2 is a top view illustrating the configuration example of the internal temperature measuring device of the first embodiment.
Figure 3:
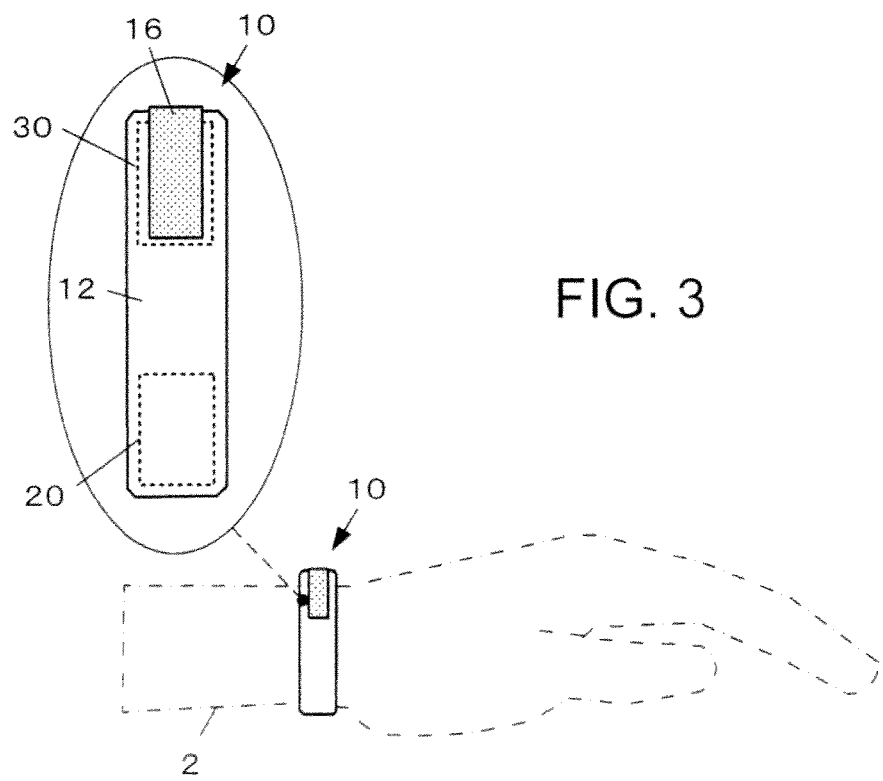
FIG. 3 is a side view illustrating the configuration example of the internal temperature measuring device of the first embodiment.

FIGS. 1 to 3 are views illustrating a configuration example of an internal temperature measuring device 10 of the present embodiment. FIG. 1 corresponds to a front view, FIG. 2 corresponds to a top view, and FIG. 3 corresponds to a side view.

The internal temperature measuring device 10 is a wrist mounting-type device having a function of measuring an internal temperature and is a wearable computer which is mounted on a wrist 2 of a testee.

Specifically, the internal temperature measuring device 10 has a measurement unit 12 having an arc shape in a frontal view, and a flexible portion 14 connecting end portions of the measurement unit 12 to each other. The internal temperature measuring device 10 in its entirety has an annular shape in a frontal view. It is favorable that the measurement unit 12 is an integral molding article formed from an elastomeric resin having a shape of the alphabet "C" in a frontal view as illustrated in FIG. 1. The flexible portion of the present embodiment is realized by adopting an elastomeric resin having flexibility, a flexible belt, or the like. The measurement unit 12 is warped due to a force caused by the flexible portion 14 tending to contract, and each of the back side inner surface and the palm side inner surface is in tight contact with the skin surface of the wrist 2.

A display section 16 and an operational input section 18 are provided on the top surface of the measurement unit 12 on the back side. A battery 20, a control substrate 30, and a pair of sensor sections configured to include a first sensor module 70A and a second sensor module 70B are internally housed inside the measurement unit 12.

The display section 16 is a display device which displays various types of information for a user. Displaying thereof is controlled through the control substrate 30. For example, the display section 16 is realized by adopting a thin-type touch panel, a liquid crystal display (LCD), an organic EL display, or the like. Particularly, it is favorable that the display section 16 is a curved-type display which is curved along the outer shape of the measurement unit 12, and it is more favorable to be a flexible-type display which can be deformed and can follow elastic deformation of the measurement unit 12.

The operational input section 18 is a device which receives an operational input conducted by a user. The operational input section 18 outputs a signal corresponding to an operational input to the control substrate 30. The example in FIGS. 1 and 2 illustrates two button switches. However, the operational input section 18 may be realized by adopting a dial, a touch pad, an acceleration sensor, or the like other than the button switches. Naturally, the number and the position of the operational input section 18 can be suitably set.

The battery 20 supplies electricity to the control substrate 30 and the like. In the present embodiment, a terminalless-type battery is adopted so as to cope with wireless power feeding. However, a connection portion with respect to a charging cable which also serves as a data cable so as to communicate with the outside may be suitably provided.

The first sensor module 70A and the second sensor module 70B are sensor sections which are in tight contact with the surface of the wrist 2 and measure a surface temperature at a contact position, and a heat flux passing through the modules, thereby outputting signals respectively corresponding to measurement values thereof to the control substrate 30.

In the present embodiment, the first sensor module 70A and the second sensor module 70B have the same structures as each other. The first sensor module 70A will be representatively described as a structural example. The sensor module has a stacked layer structure including a measurement target contact portion 71, a heat diffusion layer 72, a heat transfer layer 73, a heat flow sensor 82, a heat transfer layer 74, a heat diffusion layer 75, and an external environment contact portion 76 in order from a contact surface side with respect to a measurement target (wrist 2). A temperature sensor 80 is internally housed in the heat transfer layer 73 so as to able to measure a temperature of the heat diffusion layer 72. The heat flow sensor 82 is also internally housed therein so as to be able to measure a heat flow between the heat transfer layer 73 and the heat transfer layer 74. Signal wires 83 are respectively drawn out from the temperature sensor 80 and the heat flow sensor 82 and are connected to the control substrate 30.

The control substrate 30 is equipped with a central processing unit (CPU) 31, an IC memory 32, an input/output interface IC 34, a radio communication module 36 which establishes radio communication with respect to an external apparatus and realizes data communication. The input/output interface IC 34 controls inputting/outputting of signals between the CPU 31 and each of the sections (for example, the display section 16, the operational input section 18, the first sensor module 70A, the second sensor module 70B, and the like). The input/output interface IC 34 is an acquisition unit which acquires a temperature and a heat flux measured with the first sensor module 70A and the second sensor module 70B. When measurement of a temperature and a heat flux itself is referred to as acquisition, the first sensor module 70A and the second sensor module 70B correspond to the acquisition units.

It is favorable to adopt a flexible-type substrate as the control substrate 30. The control substrate 30 of the present embodiment causes the CPU 31 to execute a control program stored in the IC memory 32, thereby realizing various types of functions related to measurement of an internal temperature, and the like. A portion or the entirety of the control substrate 30 may be realized through an application specific integrated circuit (ASIC), a field-programmable gate array (FPGA), a system on a chip (SoC), or the like.

2: Measurement Principles

Figure 4:
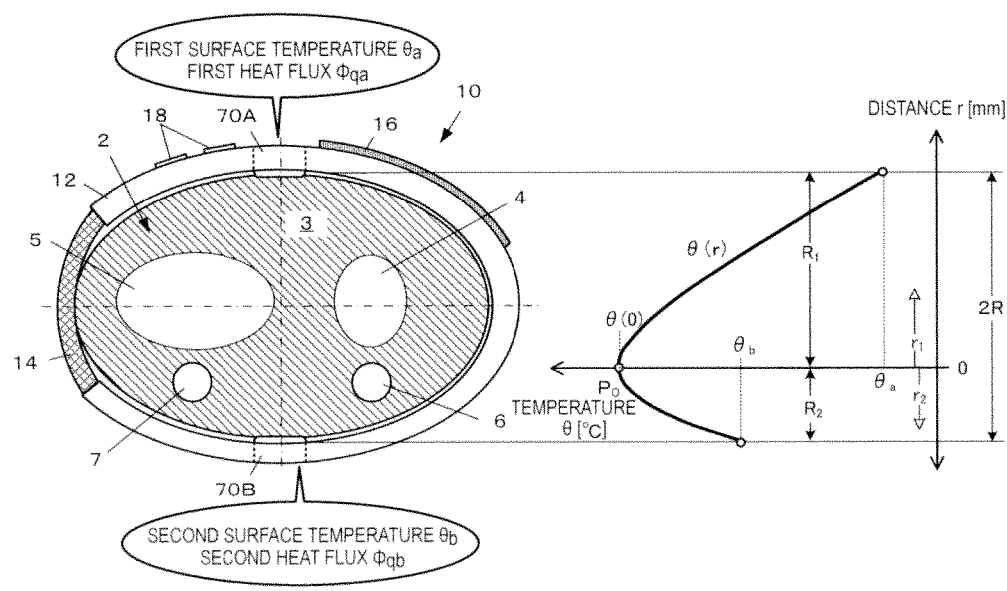
FIG. 4 is a view for describing measurement principles of measurement of an internal temperature in the first embodiment.

FIG. 4 is a view for describing measurement principles of measurement of an internal temperature in the present embodiment and illustrates a cross-sectional view in a state where the internal temperature measuring device 10 is mounted on the measurement target (in the present embodiment, the wrist 2) and a graph of an internal temperature distribution.

When the internal temperature measuring device 10 of the present embodiment is mounted on the measurement target (in the present embodiment, the wrist 2), the measurement target contact portion 71 comes into contact with the back side surface of the wrist 2 such that the first sensor module 70A can measure a first surface temperature $\theta_a$ and a first heat flux $\phi_{qa}$. Similarly, the measurement target contact portion 71 comes into contact with the palm side surface of the wrist 2 such that the second sensor module 70B can measure a second surface temperature $\theta_b$ and a second heat flux $\phi_{qb}$. The back side surface is an example of a one side surface, and the palm side surface is an example of an opposite side surface. The first surface temperature $\theta_a$ and the first heat flux $\phi_{qa}$ are respectively examples of a one side temperature and a one side heat flux, and the second surface temperature $\theta_b$ and the second heat flux $\phi_{qb}$ are respectively examples of an opposite side temperature and an opposite side heat flux.

There is biasing in a heat source position which is present inside the wrist 2. In other words, there are an ulna 4 and a radius 5 in the vicinity of a substantial center in a direction connecting the back side and the palm side (hereinafter, will be referred to as "back/palm direction" or "display direction") of the wrist 2 (substantial center in the vertical direction in FIG. 4), and there are an ulnar artery 6 and a radial artery 7 on the palm side of the ulna 4 and the radius 5. As a heat source in the wrist 2, heat generation of tissue 3 such as muscle is naturally included and arterial blood flowing in the ulnar artery 6 and the radial artery 7 significantly serves as the heat source. Therefore, as illustrated in the graph, a highest temperature point $P_0$ (point indicating a temperature to be measured by the internal temperature measuring device 10) in the internal temperature distribution is at a position which is offset from the center to the palm side in the back/palm direction.

Here, a coordinate axis of a distance r along the back/palm direction (front/back direction) of the wrist 2 is set while having the highest temperature point $P_0$ in the internal temperature distribution as the origin of coordinates, and a function of the internal temperature distribution $\theta(r)$ in which the distance r is a variable is postulated. Consequently, as indicated with the bold line in the graph, an internal temperature $\theta(0)$ is pointed by the highest temperature point $P_0$ in the internal temperature distribution, and the internal temperature and the heat flux of the wrist 2 are gradually lowered toward the surface. The surface position (distance $R_1$) on the back side exhibits the first surface temperature $\theta_a$ and the first heat flux $\phi_{qa}$. The surface position (distance $R_2$) on the palm side exhibits the second surface temperature $\theta_b$ and the second heat flux $\phi_{qb}$.

Here, the distance $R_1$ is a depth of the highest temperature point $P_0$ in the internal temperature distribution viewed from the first sensor module 70A, and the distance $R_2$ is a depth of the highest temperature point $P_0$ in the internal temperature distribution viewed from the second sensor module 70B. In other words, the sum of the distance $R_1$ and the distance $R_2$ is equal to a thickness "2R" in the back/palm direction (front/back direction) of a wrist. The thickness "2R" of a wrist is a value which is separately and clearly measured by a user before the measurement.

Accordingly, the distance $R_1$ and the distance $R_2$ are unknowns. However, the unknowns are obtained by applying boundary conditions established based on four measurement results obtained based on a function of the internal temperature distribution, and the condition of $R_1+R_2=2R$. In other words, the function of the internal temperature distribution is obtained, and thus, the internal temperature $\theta(0)$ at the highest temperature point $P_0$ can be obtained from the measurement result based on the function of the internal temperature distribution.

The measurement principles will be more specifically described as follows.

As an equation of heat conductivity in a living body describing a heat model of the living body, while a measurement site in the four limbs or the like is postulated to have a cylindrical shape, it is possible to consider an equation of heat conductivity in the cylinder, to which a member for thermogenesis caused due to metabolism of site tissue and a member for a heat inflow from arterial blood in the site to the site tissue are added. Accordingly, while a thermal phenomenon of the living body is considered to be a steady state, the equation of heat conductivity in the living body can be described through Expression (1) by applying a cylindrical coordinate system.

$$\lambda \frac{1}{r}\frac{\partial}{\partial r}r\left(\frac{\partial \theta}{\partial r}\right) + M + K(\theta_{ar} - \theta) = 0 \quad \text{Expression (1)}$$

$\theta°$ C.: temperature of tissue
$\theta_{ar}°$ C.: temperature of arterial blood
r m: distance from center axis in cylindrical coordinate system
$\lambda$ W/(m×k): heat conductivity of tissue
M W/m$^3$: quantity of thermogenesis caused due to metabolism
K W/(m$^3$×K): blood-flow heat proportionality constant In Expression (1), the first member on the left side expresses a general heat conductivity equation (that is, diffusion equation), the second member expresses the quantity of thermogenesis caused due to metabolism, and the third member expresses a heat inflow from arterial blood to site tissue. The equation of heat conductivity in a living body indicated through Expression (1) describes a state where an arterial blood vessel is hypothetically and equally diffused in tissue, thereby being able to be also referred to as a lumped constant model.

The heat inflow from arterial blood to tissue expressed in the third member on the left side varies depending on the temperature of the tissue. However, macroscopically, the heat inflow from arterial blood to tissue can be set to a constant value. Accordingly, Expression (1) can be more simply solved as a heat conduction model of constant heat generation. Specifically, a blood-flow heat proportionality constant K can be expressed through the product of a blood density $\rho_b$, specific heat $C_b$ at constant pressure, and a blood flow rate $w_b$ per unit volume. Therefore, similar to thermogenesis caused due to metabolism, Expression (1) can be described as Expression (2) by setting the third member on the left side in Expression (1) to a heat generation value W W/m$^3$ which is not present in the temperature.

$$\lambda \frac{1}{r}\frac{\partial}{\partial r}r\left(\frac{\partial \theta}{\partial r}\right) + M + W = 0 \quad \text{Expression (2)}$$

In this case, the heat inflow from arterial blood to tissue is proportion to the blood flow rate. Therefore, Expression (2) can be described as Expression (3).

$$W = k \cdot \rho_b \cdot C_b \cdot w_b \quad \text{Expression (3)}$$

$\rho_b$ kg/m$^3$: density of blood
$c_b$ J/(kg×K): specific heat at constant pressure in blood
$w_b$ m$^3$/(m$^3$×s): blood flow rate per unit volume
k: proportionality constant In Expression (4), a temperature distribution $\theta(r)$ is set to a surface temperature $\theta(R)$.

$$\theta(r) = \theta(R) + \frac{1}{4}\frac{M+W}{\lambda}(R^2 - r^2) \quad \text{Expression (4)}$$

Here, the internal temperature is observed through the first sensor module 70A and the second sensor module 70B. The distance of the highest temperature point $P_0$ in the internal temperature distribution is set to "0", and the distances from the highest temperature point $P_0$ to the surfaces are respectively referred to as $r_1$ and $r_2$ (refer to FIG. 4). The internal temperature distributions observed from the first sensor module 70A and the second sensor module 70B are respectively described as $\theta_a(r_1)$ and $\theta_b(r_2)$, and thus, Expressions (5) and (6) can be obtained from Expression (4).

$$\theta_a(r_1) = \theta_a(R_1) + \frac{1}{4}\frac{M+W}{\lambda}(R_1^2 - r_1^2) \quad \text{Expression (5)}$$

$$\theta_b(r_2) = \theta_b(R_2) + \frac{1}{4}\frac{M+W}{\lambda}(R_2^2 - r_2^2) \quad \text{Expression (6)}$$

The internal temperatures $\theta_a(0)$ and $\theta_b(0)$ which are the highest temperature points $P_0$ in the internal temperature distribution respectively observed from the first sensor module 70A and the second sensor module 70B are $r_1 = 0$ and $r_2 = 0$ in Expressions (5) and (6), thereby being able to be expressed through Expressions (7) and (8).

$$\theta_a(0) = \theta_a(R_1) + \frac{1}{4}\frac{M+W}{\lambda}R_1^2 \quad \text{Expression (7)}$$

$$\theta_b(0) = \theta_b(R_2) + \frac{1}{4}\frac{M+W}{\lambda}R_2^2 \quad \text{Expression (8)}$$

The internal temperatures $\theta_a(0)$ and $\theta_b(0)$ are surface temperatures respectively measured with the first sensor module 70A and the second sensor module 70B. In other words, Expressions (9) and (10) are established as the boundary conditions.

$$\theta_a(R_1) = \theta_a \quad \text{Expression (9)}$$

$$\theta_b(R_2) = \theta_b \quad \text{Expression (10)}$$

Since the internal temperatures of a living body, that is, the highest temperature points $P_0$ in the internal temperature distribution coincide with each other when observed from the first sensor module 70A and the second sensor module 70B, when the internal temperature is referred to as $\theta(0)$, Expression (11) is established as the boundary conditions.

$$\theta(0) = \theta_a(0) = \theta_b(0) \quad \text{Expression (11)}$$

Here, returning to Expression (4), the focus will be on the heat flux.

When Expression (4) is differentiated by the distance r, and the heat conductivity $\lambda$ of tissue is integrated, a heat flux distribution can be obtained as in Expression (12).

$$\phi_q(r) = \lambda \frac{\partial}{\partial r}\theta(r) = -\frac{1}{2}(M+W)r \quad \text{Expression (12)}$$

Similarly, when Expressions (5) and (6) are differentiated by the distance r, and the results are respectively referred to as r=r1 and r=r2, the heat fluxes observed from the first sensor module 70A and the second sensor module 70B can be described as Expressions (13) and (14).

$$\phi_{q_a}(r_1) = \lambda \frac{\partial}{\partial r}\theta_a(r_1) = -\frac{1}{2}(M+W)r_1 \qquad \text{Expression (13)}$$

$$\phi_{q_b}(r_2) = \lambda \frac{\partial}{\partial r}\theta_b(r_2) = -\frac{1}{2}(M+W)r_2 \qquad \text{Expression (14)}$$

Meanwhile, when $r=R_1$ in Expression (12), the first heat flux $\phi_{q_a}$ measured with the first sensor module 70A is obtained. When $r=R_2$ in Expression (12), the second heat flux $\phi_{q_b}$ measured with the second sensor module 70B is obtained. Accordingly, Expressions (15) and (16) are respectively induced from Expressions (13) and (14).

$$|\phi_{q_a}(R_1)|=1/2(M+W)R_1=\phi_{q_a} \qquad \text{Expression (15)}$$

$$|\phi_{q_b}(R_2)|=1/2(M+W)R_2=\phi_{q_b} \qquad \text{Expression (16)}$$

As illustrated in the graph of FIG. 4, the sum of the depth $R_1$ and the depth $R_2$ to the highest temperature point $P_0$ observed from the first sensor module 70A and the second sensor module 70B is equal to the diameter of the measurement target, in this case, the thickness "2R" from the back side to the palm side of the wrist 2. Accordingly, Expression (17) is established.

$$R_1+R_2=2R \qquad \text{Expression (17)}$$

When Expressions (7) to (17) are set in a simultaneous form, and the internal temperature θ(0) at the highest temperature point $P_0$ in the internal temperature distribution is solved, Expression (18) can be obtained. The sign λ in Expression (18) indicates heat conductivity of a living body, and a statistic is applied thereto in the present embodiment.

$$\theta(0) = \frac{\theta_a\phi_{qb}+\theta_b\phi_{qa}}{\phi_{qa}+\phi_{qb}} + \frac{R}{2\lambda}\frac{\phi_{qb}\phi_{qa}}{\phi_{qa}+\phi_{qb}} \qquad \text{Expression (18)}$$

Accordingly, even though each of the depth $R_1$ and the depth $R_2$ to the highest temperature point $P_0$ observed from the first sensor module 70A and the second sensor module 70B is undefined, the temperature, that is, the internal temperature θ(0) at the highest temperature point $P_0$ in the internal temperature distribution can be measured based on the first surface temperature $\theta_a$ and the first heat flux $\phi_{qa}$ measured with the first sensor module 70A, the second surface temperature $\theta_b$ and the second heat flux $\phi_{qb}$ measured with the second sensor module 70B, and the thickness of the measurement target (the thickness "2R" from the backside to the palm side of the wrist 2).

Expression (18) is established not only in a case where the depth $R_1$ and the depth $R_2$ are undefined but also in a case where the depth $R_1$ and the depth $R_2$ fluctuate. In other words, even in a case where maldistribution of the heat source varies in the measurement target and the highest temperature point $P_0$ of the internal temperature varies, the internal temperature of a living body, that is, the highest temperature point in the internal temperature distribution can be measured.

3: Processing Flow

Figure 5:
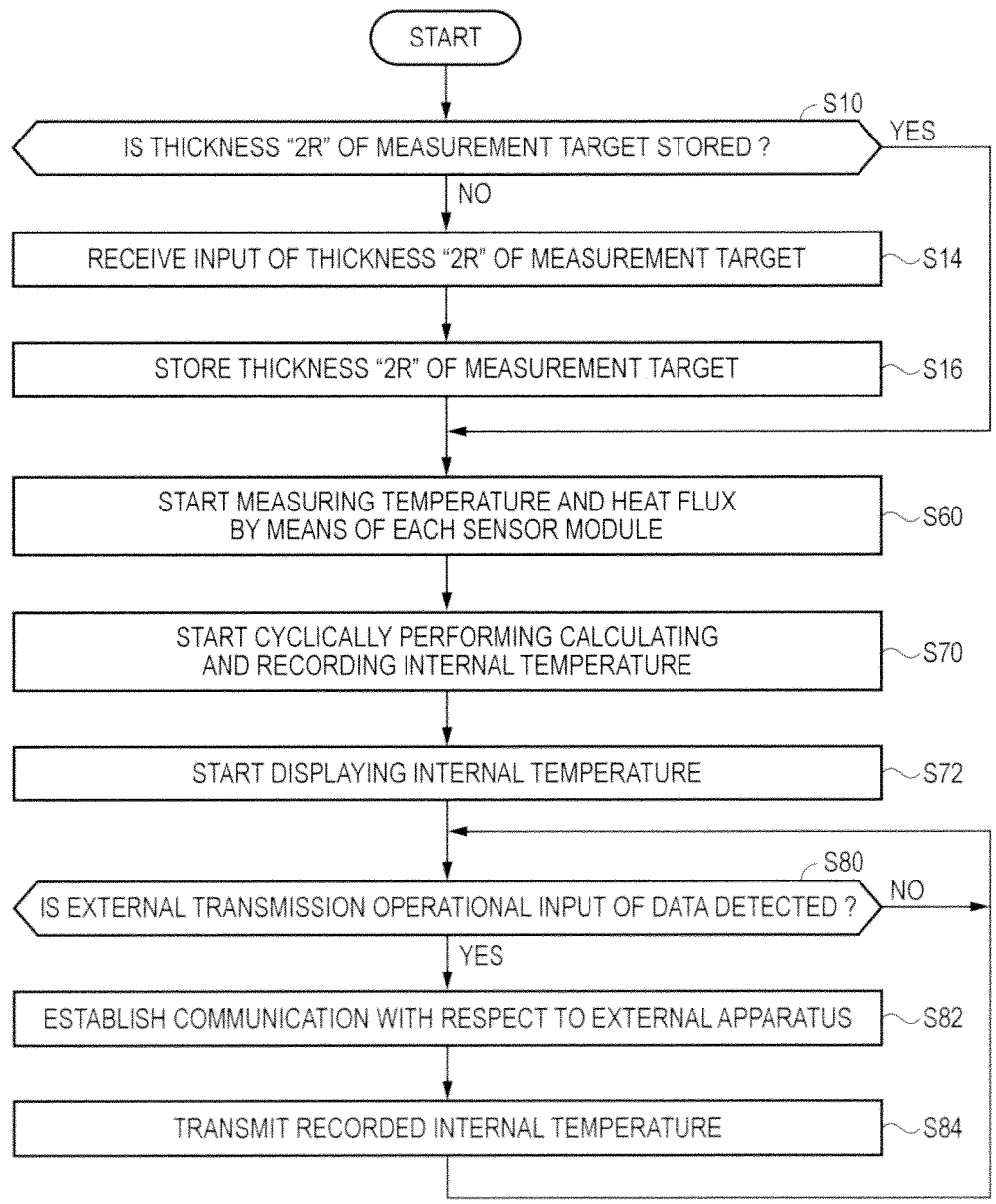
FIG. 5 is a flow chart for describing a processing flow of the internal temperature measuring device of the first embodiment.

FIG. 5 is a flow chart for describing a processing flow of the internal temperature measuring device 10 of the present embodiment. The processing flow is conducted when the CPU 31 of the control substrate 30 reads out a predetermined program stored in the IC memory 32 and executes the program. The control substrate 30 utilizes an internal clock so as to clock the current date and time.

Before measurement starts, the internal temperature measuring device 10 checks whether or not the thickness "2R" of the measurement target is recorded in a predetermined storage domain of the IC memory 32. If the thickness "2R" is not stored therein (NO in Step S10), processing of receiving an input of the thickness "2R" of the measurement target is executed (Step S14), and the input value is stored as the thickness "2R" of the measurement target (Step S16).

The internal temperature measuring device 10 can receive a reset operation in which a separately stored value of the thickness "2R" of the measurement target is reset.

When the thickness "2R" of the measurement target is stored, the internal temperature measuring device 10 starts measuring the surface temperature and the heat flux by means of the sensor modules (Step S60). In the present embodiment, the first surface temperature $\theta_a$ and the first heat flux $\phi_{qa}$ start to be measured with the first sensor module 70A, and the second surface temperature $\theta_b$ and the second heat flux $\phi_{qb}$ start to be measured with the second sensor module 70B.

Subsequently, the internal temperature measuring device 10 performs substitution of four measurement values such as the first surface temperature $\theta_a$, the first heat flux $\phi_{qa}$, the second surface temperature $\theta_b$, and the second heat flux $\theta_{qb}$ in Expression (18) at a predetermined cycle, and calculates the internal temperature, thereby starting recording processing while causing the result to match the current date and time (Step S70). Processing of causing the display section 16 to display the latest internal temperature starts (Step S72).

In a case where a predetermined external transmission operational input in which recorded data of the internal temperature is transmitted to an external apparatus (for example, a computer for accumulating and analyzing data) is detected (YES in Step S80), the internal temperature measuring device 10 establishes communication with respect to the external apparatus through the radio communication module 36 (Step S82), and the internal temperature measuring device 10 transmits the data of the internal temperature stored in the IC memory 32 to the external apparatus (Step S84).

Hereinbefore, according to the present embodiment, since the internal temperature measuring device 10 is a wrist mounting-type device, convenience and comfort of measurement can be ensured. The results measured in the front (the one side surface side) and the back (the opposite side surface side) of the measurement target are considered to be manifestation at the surface position in the internal temperature distribution. Therefore, it is possible to measure the internal temperature in which the influences of an error caused due to the shape of the measurement target and an error caused due to biasing of the heat source position inside the measurement target is minimally restrained.

In the present embodiment, the thickness "2R" from the back side to the palm side of the wrist 2 is configured to be measured by a user in advance and to be input and set before measurement. However, the embodiment is not limited thereto. For example, statistics of the thickness "2R" in groups different from each other based on age, weight, height, gender, and the like may be stored in the IC memory 32 in advance. Then, in place of Steps S10 to S16, the embodiment may be configured to execute a step in which a user inputs age, weight, height, gender, and the like before measurement, and a step in which "2R" is read out from the statistics of the groups suitable for the values, after the inputting.

Second Embodiment

Next, description will be given regarding a second embodiment of the invention is applied.

Basically, the present embodiment is realized in a manner similar to that of the first embodiment. However, there is a difference in the structure of the device, disposition of the sensor module, and a process of calculating an internal temperature. Hereinafter, the difference with respect to the first embodiment will be mainly described, and the same reference signs as in the first embodiment will be applied to the configuration elements similar to those of the first embodiment, thereby omitting the description thereof.

Figure 6:
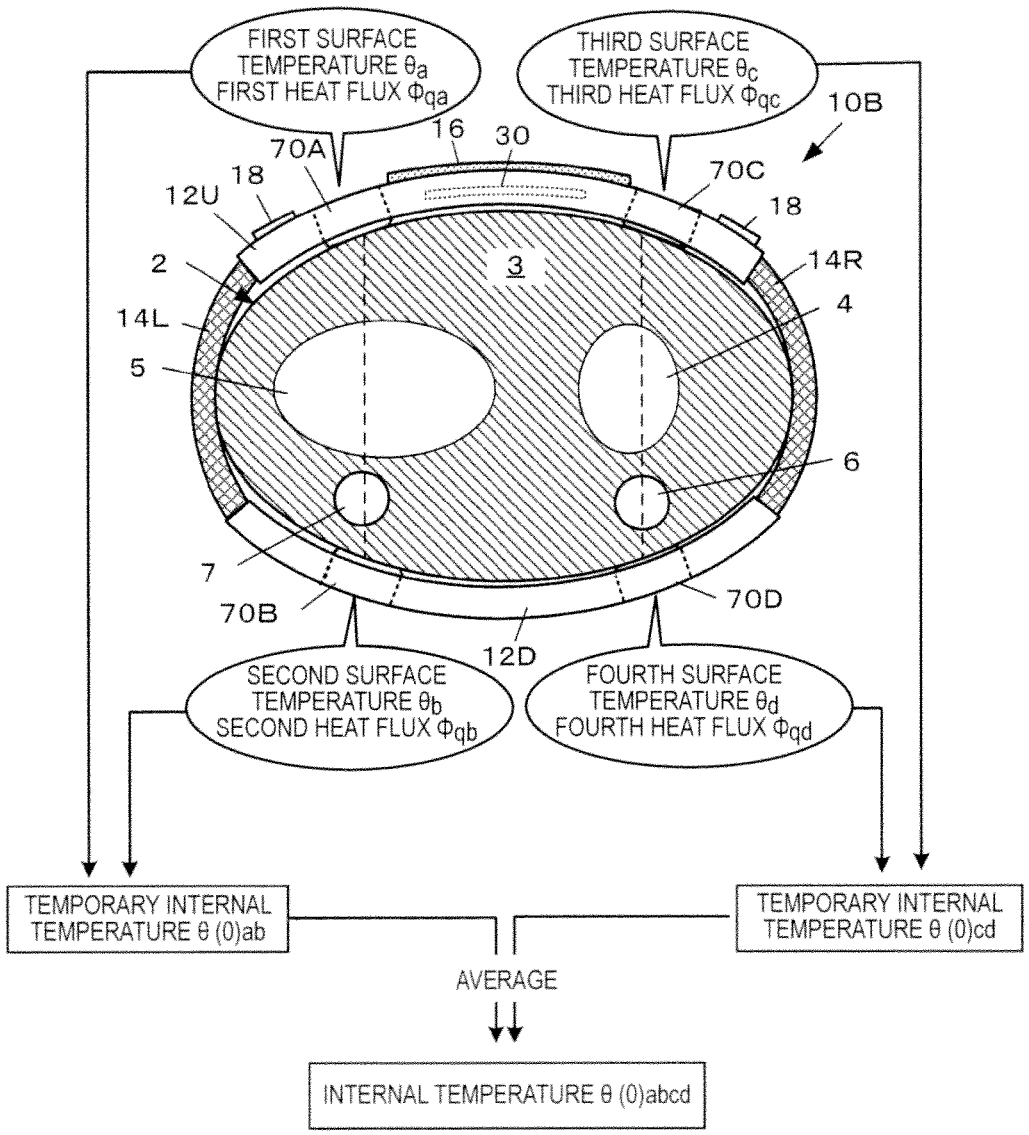
FIG. 6 is a front view illustrating a configuration example of an internal temperature measuring device of a second embodiment.

FIG. 6 is a front view illustrating a configuration example of an internal temperature measuring device 10B of the present embodiment and illustrates a view for describing the process of calculating an internal temperature.

In the internal temperature measuring device 10B, an arc-shaped back side measuring unit 12U and an arc-shaped palm side measuring unit 12D are disposed such that recess portions thereof face each other, and sets of end portions thereof facing each other are respectively interlocked with each other through a first flexible portion 14L or a second flexible portion 14R. Accordingly, the internal temperature measuring device 10B in its entirety has an annular shape in a frontal view.

The back side measuring unit 12U includes the display section 16, the operational input section 18, the control substrate 30, the first sensor module 70A, and a third sensor module 70C.

The palm side measuring unit 12D has the second sensor module 70B and a fourth sensor module 70D.

Each of the first sensor module 70A to the fourth sensor module 70D has a configuration similar to that of the first embodiment (refer to FIG. 1).

The first sensor module 70A and the second sensor module 70B configure a first pair of sensor sections and are disposed while having a positional relationship interposing the radial artery 7 which is positioned at a first internal position. The first sensor module 70A measures the first surface temperature $\theta_a$ and the first heat flux $\phi_{qa}$, and the second sensor module 70B measures the second surface temperature $\theta_b$ and the second heat flux $\phi_{qb}$.

The third sensor module 70C and the fourth sensor module 70D configure a second pair of sensor sections and are disposed while having a positional relationship interposing the ulnar artery 6 which is positioned at a second internal position. The third sensor module 70C measures a third surface temperature $\theta_c$ and a third heat flux $\phi_{qc}$, and the fourth sensor module 70D measures a fourth surface temperature $\theta_d$ and a fourth heat flux $\phi_{qd}$.

The internal temperature measuring device 10B of the present embodiment calculates a temporary internal temperature $\theta(0)_{ab}$ and a temporary internal temperature $\theta(0)_{cd}$ for each pair of sensor sections and calculates a final internal temperature $\theta(0)_{abcd}$ based on the average value of the temporary internal temperatures.

Figure 7:
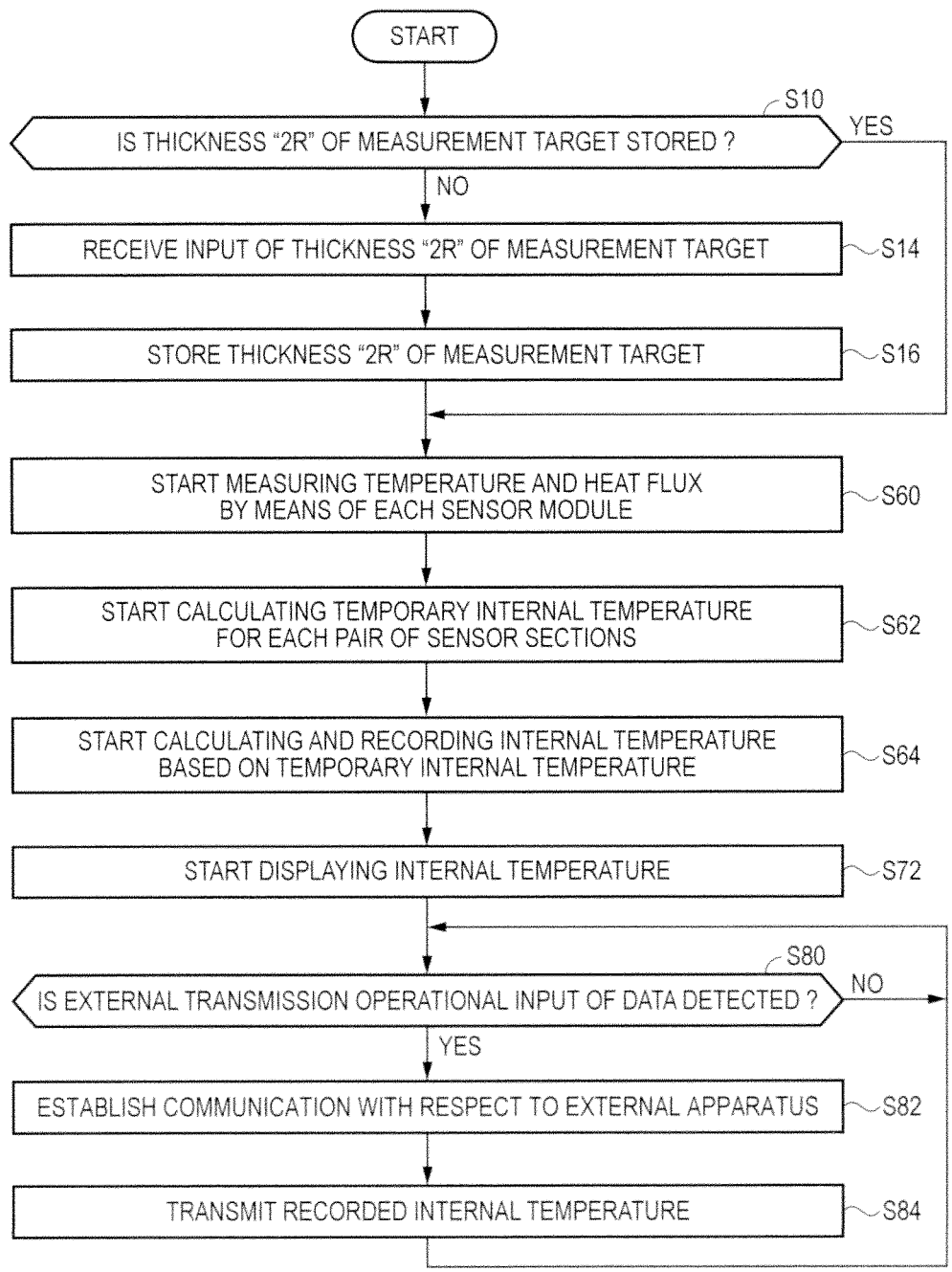
FIG. 7 is a flow chart for describing a processing flow of the internal temperature measuring device of the second embodiment.

FIG. 7 is a flow chart for describing a processing flow of the internal temperature measuring device 10B of the present embodiment. The processing flow of the present embodiment basically has a flow similar to that of the first embodiment. However, Steps S62 to S64 are executed subsequently to Step S60, and Step S70 is omitted.

In other words, subsequently to Step S60, the internal temperature measuring device 10B calculates the temporary internal temperature $\theta(0)_{ab}$ through Expression (18) based on the first surface temperature $\theta_a$ and the first heat flux $\phi_{qa}$ measured with the first sensor module 70A, and the second surface temperature $\theta_b$ and the second heat flux $\phi_{qb}$ measured with the second sensor module 70B. The internal temperature measuring device 10B starts calculating the temporary internal temperature $\theta(0)_{cd}$ through Expression (18) by means of the second pair of sensor sections, based on the third surface temperature $\theta_c$ and the third heat flux $\phi_{qc}$ measured with the third sensor module 70C, and the fourth surface temperature $\theta_d$ and the fourth heat flux $\phi_{qd}$ measured with the fourth sensor module 70D (Step S62).

Subsequently, the internal temperature measuring device 10B calculates the final internal temperature $\theta(0)_{abcd}$ based on the average value of the temporary internal temperature $\theta(0)_{ab}$ and the temporary internal temperature $\theta(0)_{cd}$, and starts processing of storing the result in the IC memory 32 while causing the result to match the measurement date and time (Step S64).

According to the present embodiment, it is possible to obtain an effect similar to that of the first embodiment. Even though there are demerits such as an increase of the manufacturing cost caused due to the complicated structure of the device, the doubled number of sensor modules to be equipped with, and the like, there are merits in that the internal temperature can be more precisely measured by virtue of increased measurement data. Specifically, it is possible to further reduce a measurement error caused due to individual differences in positions of the ulnar artery 6 and the radial artery 7.

Third Embodiment

Next, description will be given regarding a third embodiment of the invention is applied.

Basically, the present embodiment is realized in a manner similar to that of the first embodiment. However, there is a difference in the structure of the device, disposition of the sensor module, and the process of calculating an internal temperature. Hereinafter, the difference with respect to the first embodiment will be mainly described, and the same reference signs as in the first embodiment will be applied to the configuration elements similar to those of the first embodiment, thereby omitting the description thereof.

Figure 8:
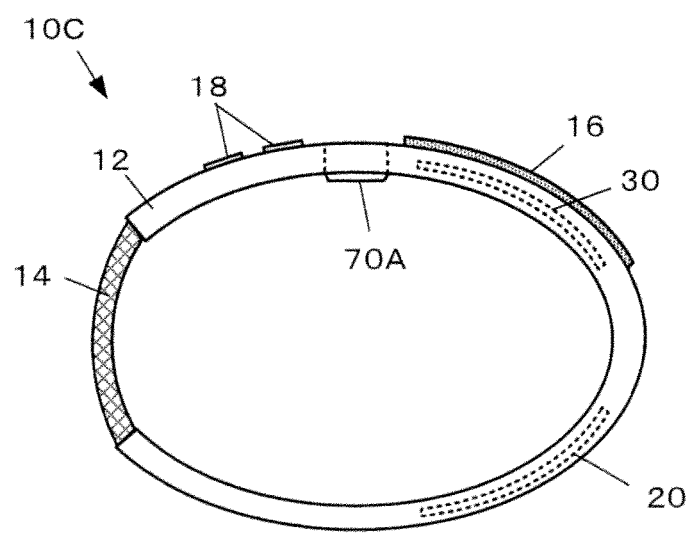
FIG. 8 is a front view illustrating a configuration example of an internal temperature measuring device of a third embodiment.

FIG. 8 is a front view illustrating a configuration example of an internal temperature measuring device 10C of the present embodiment.

Basically, in the internal temperature measuring device 10C, compared to the internal temperature measuring device 10 of the first embodiment, the second sensor module 70B is omitted.

Figure 9:
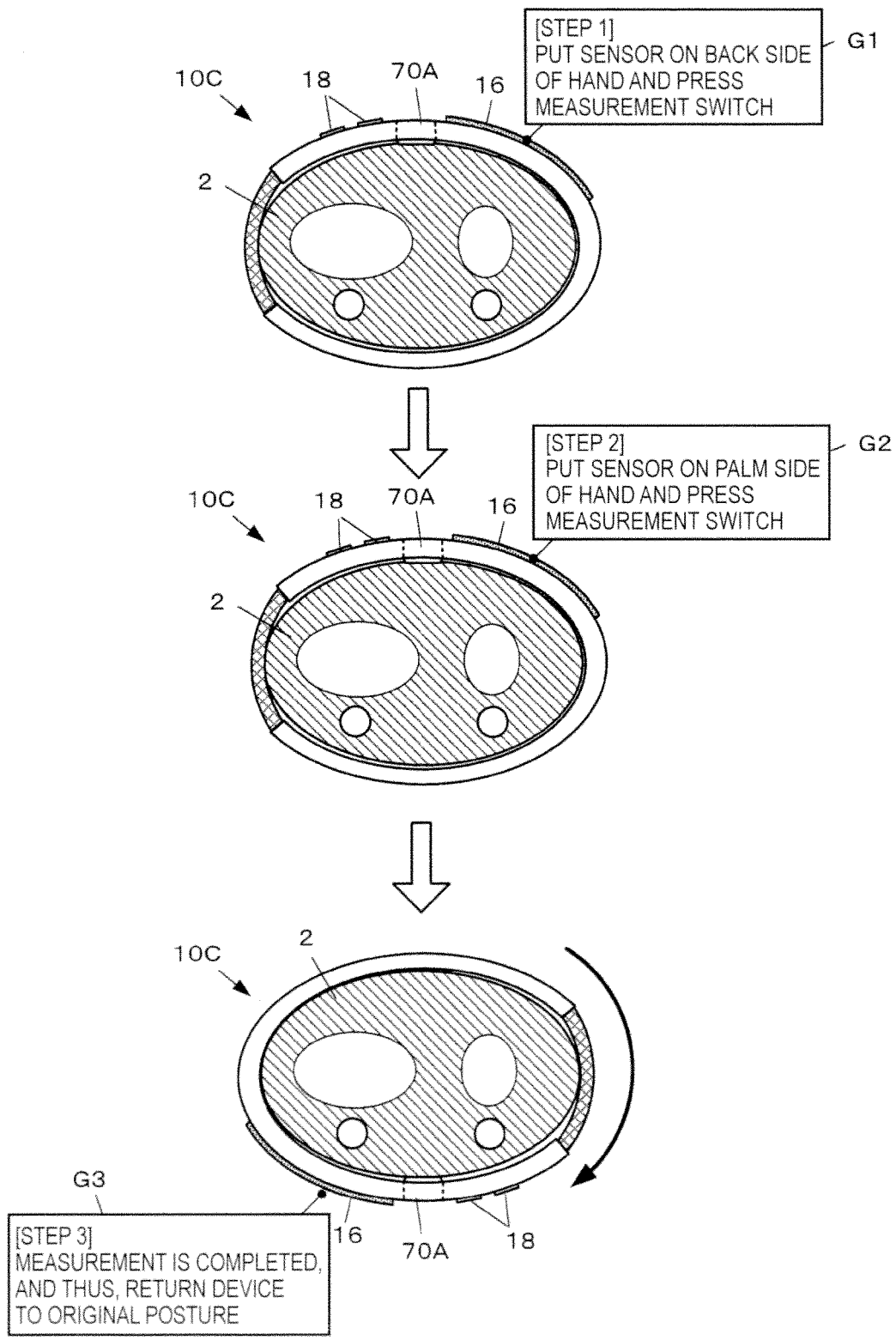
FIG. 9 is a view for describing a procedure of measuring an internal temperature in the third embodiment.

FIG. 9 is a view for describing a procedure of measuring an internal temperature in the present embodiment.

In the first embodiment, when the internal temperature measuring device 10 is worn and kept on a wrist, the internal temperature is automatically measured and stored. However, in the present embodiment, a user carries out work of inverting a mounting posture of the internal temperature measuring device 10C every time measuring the internal temperature so as to change a relative disposition position with respect to the measurement target of the first sensor module 70A.

In other words, when the measurement time comes, the internal temperature measuring device 10C causes the display section 16 to display a first operational guide G1. The first operational guide G1 has contents of urging a user to check for the first sensor module 70A positioned on the back side (the one side surface side) of the wrist and to operate a predetermined operational input section 18. When an operation of the predetermined operational input section 18 is detected, the internal temperature measuring device 10C measures the surface temperature and the heat flux and stores the results as the first surface temperature $\theta_a$ and the first heat flux $\phi_{qa}$ respectively.

When the first surface temperature $\theta_a$ and the first heat flux $\phi_{qa}$ are stored, the internal temperature measuring device 10C causes the display section 16 to display a second operational guide G2 such that the first sensor module 70A is positioned on the palm side (the opposite side surface side) of the wrist. The second operational guide G2 has contents of urging the user to change the mounting posture of the device and to operate a predetermined operational input section 18. When an operation of the predetermined operational input section 18 is detected, the internal temperature measuring device 10C measures the surface temperature and the heat flux and stores the results as the second surface temperature $\theta_b$ and the second heat flux $\phi_{qb}$ respectively.

When the second surface temperature $\theta_b$ and the second heat flux $\phi_{qb}$ are stored, since the measurement is completed, the internal temperature measuring device 10C causes the display section 16 to display a third operational guide G3 for a certain time so as to urge the user to return the device to the original mounting posture.

Figure 10:
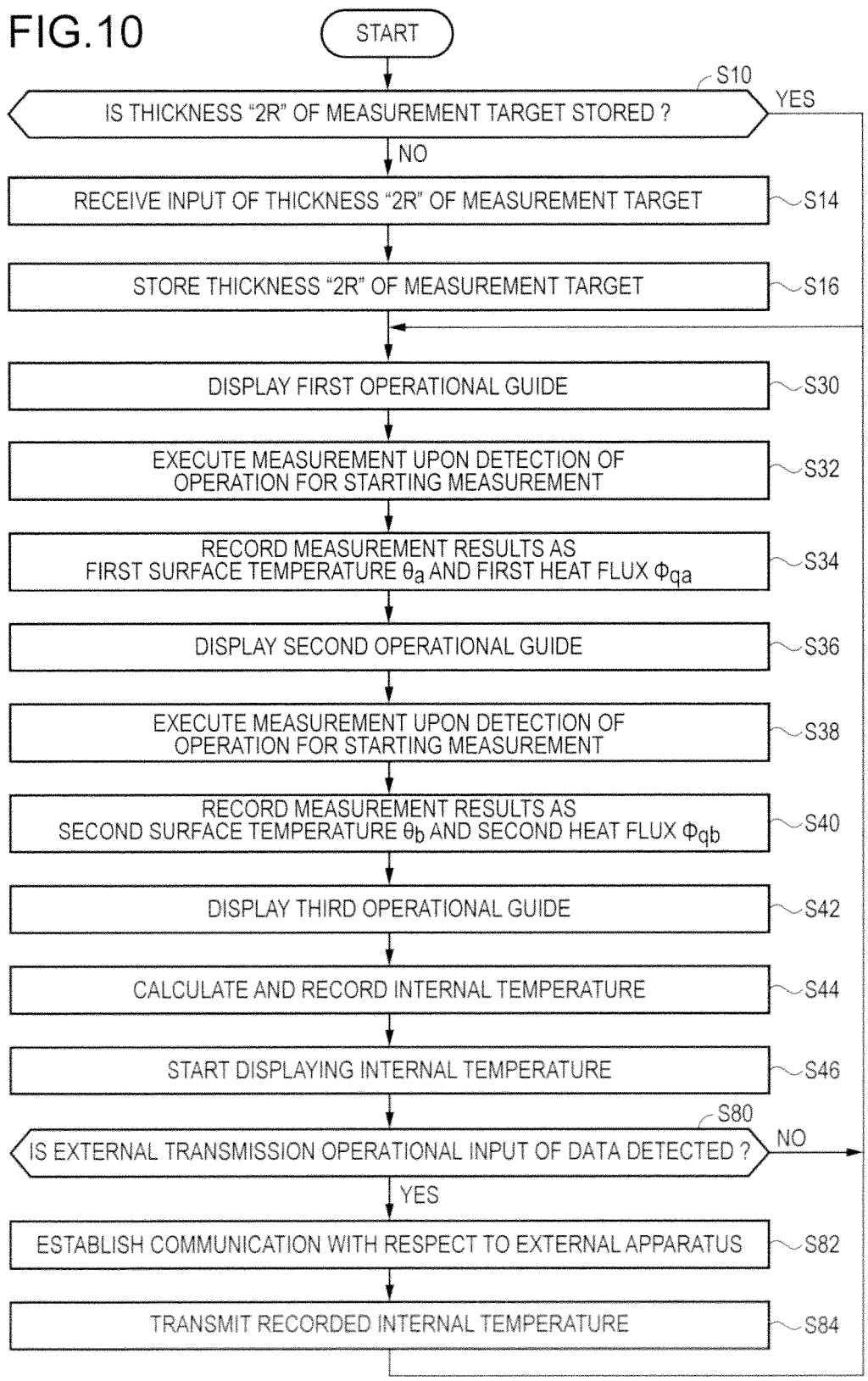
FIG. 10 is a flow chart for describing a processing flow of the internal temperature measuring device of the third embodiment.

FIG. 10 is a flow chart for describing a processing flow of the internal temperature measuring device 10C of the present embodiment. The processing flow of the present embodiment basically has a flow similar to that of the first embodiment. However, Steps S30 to S46 are executed subsequently to Step S16, and Steps S60 to S72 are omitted.

Specifically, the internal temperature measuring device 10C causes the display section 16 to display the first operational guide G1 (Step S30). When an operation of starting measurement performed with respect to a predetermined operational input section 18 is detected, the internal temperature measuring device 10C executes measurement with the first sensor module 70A (Step S32) and stores the measurement results in the IC memory 32 as the first surface temperature $\theta_a$ and the first heat flux $\phi_{qa}$ respectively (Step S34).

Subsequently, the internal temperature measuring device 10C causes the display section 16 to display the second operational guide G2 (Step S36). When an operation of starting measurement performed with respect to a predetermined operational input section 18 is detected, the internal temperature measuring device 10C executes measurement with the first sensor module 70A again (Step S38) and stores the measurement results in the IC memory 32 as the second surface temperature $\theta_b$ and the second heat flux $\phi_{qb}$ respectively (Step S40).

Subsequently, the internal temperature measuring device 10C causes the display section 16 to display the third operational guide G3 (Step S42). The first surface temperature $\theta_a$ and the first heat flux $\phi_{qa}$, and the second surface temperature $\theta_b$ and the second heat flux $\phi_{qb}$ are substituted in Expression (18), and the internal temperatures are calculated. The results are stored in the IC memory 32 so as to match the measurement date and time (Step S44). Then, processing of causing the display section 16 to display the calculated internal temperatures is performed (Step S46).

According to the present embodiment, it is possible to obtain an effect similar to that of the first embodiment. Since it is troublesome for a user to additionally perform changing of the mounting posture of the internal temperature measuring device 10C, the present embodiment is inferior to the first embodiment in regard to the point of convenience in measurement. However, since the number of sensor modules to be equipped with can be reduced, there are merits of reducing the manufacturing cost.

The present embodiment can also be applied to the second embodiment.

In other words, the second sensor module 70B and the fourth sensor module 70D which the palm side measuring unit 12D is equipped with in the second embodiment are omitted. In Step S32, measurement is executed with each of the first sensor module 70A and the third sensor module 70C. In Step S34, the measurement results obtained with the first sensor module 70A are respectively referred to as the first surface temperature $\theta_a$ and the first heat flux $\phi_{qa}$, and the measurement results obtained with the third sensor module 70C are respectively referred to as the third surface temperature $\theta_c$ and the third heat flux $\phi_{qc}$. In Step S38, measurement is executed again with each of the first sensor module 70A and the third sensor module 70C. In Step S34, the measurement results obtained with the first sensor module 70A are respectively referred to as the fourth surface temperature $\theta_d$ and the fourth heat flux $\phi_{qd}$, the measurement results obtained with the third sensor module 70C are respectively referred to as the second surface temperature $\theta_b$ and the second heat flux $\phi_{qb}$, and the results are stored. In Step S44, similar to the second embodiment, a first temporary internal temperature is calculated based on the first surface temperature $\theta_a$, the first heat flux $\phi_{qa}$, the second surface temperature $\theta_b$, and the second heat flux $\phi_{qb}$, and a second temporary internal temperature is calculated based on the third surface temperature $\theta_c$, the third heat flux $\phi_{qc}$, the fourth surface temperature $\theta_d$, and the fourth heat flux $\phi_{qd}$. The final internal temperature may be configured to be calculated based on the results thereof.

Fourth Embodiment

Next, description will be given regarding a fourth embodiment of the invention is applied.

Basically, the present embodiment is realized in a manner similar to that of the first embodiment. However, there is a difference in that an external apparatus calculates the internal temperature. Hereinafter, the difference with respect to the first embodiment will be mainly described, and the same reference signs as in the first embodiment will be applied to the configuration elements similar to those of the first embodiment, thereby omitting the description thereof.

Figure 11:
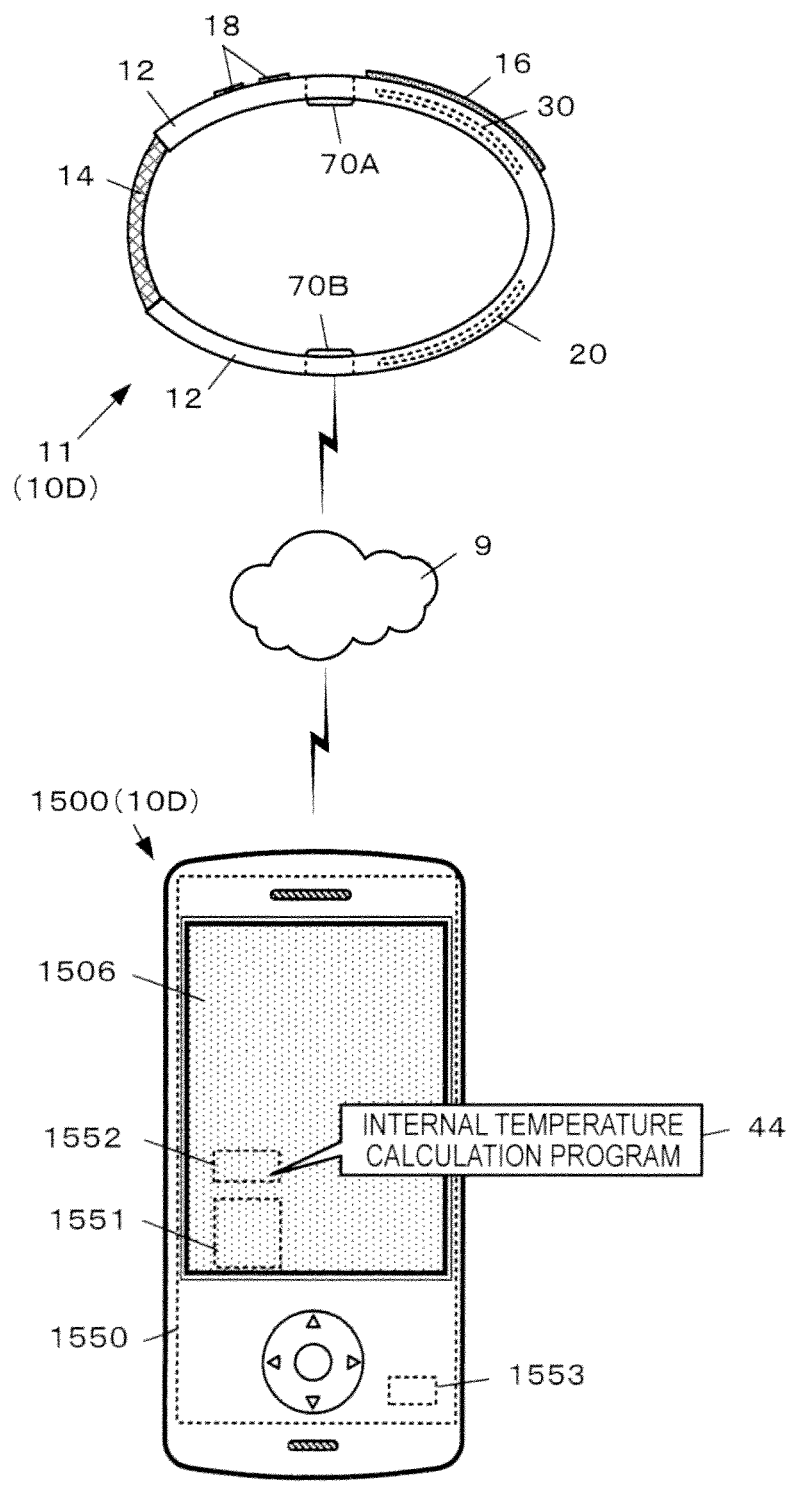
FIG. 11 is a view illustrating a configuration example of an internal temperature measuring device of a fourth embodiment.

FIG. 11 is a view illustrating a configuration example of an internal temperature measuring device 10D of the present embodiment. The internal temperature measuring device 10D has a mounting instrument 11 and a main body device 1500 which are connected to each other through a communication line 9 so as to be able to perform data communication therebetween.

The mounting instrument 11 is realized in a manner similar to that of the internal temperature measuring device 10 of the first embodiment. However, the mounting instrument 11 does not calculate the internal temperature and transmits the measurement result to the main body device 1500.

The main body device 1500 is a computer which can execute an internal temperature calculation program as an application program. In the present embodiment, a smart phone serves as the main body device 1500. However, a different form such as a personal computer and a tablet-type computer may be adopted. In other words, in the main body device 1500, communication with respect to the mounting instrument 11 is established through a radio communication module 1553 which a control substrate 1550 is equipped with, an internal temperature calculation program 44 stored in an IC memory 1552 is executed by a CPU 1551, and the internal temperature is calculated through Expression (18) based on the measurement results received from the mounting instrument 11.

Figure 12:
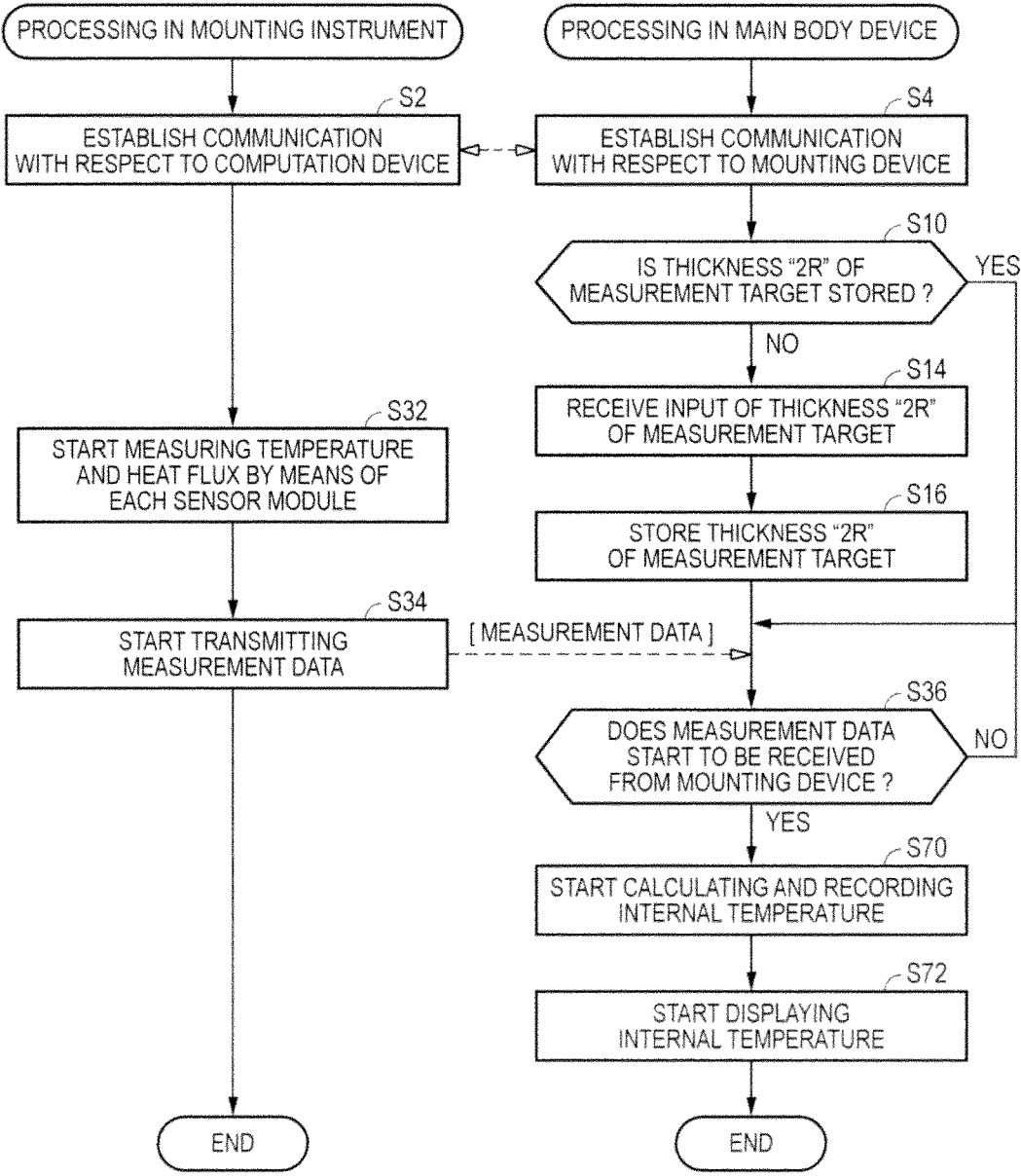
FIG. 12 is a flow chart for describing a processing flow of the internal temperature measuring device of the fourth embodiment.

FIG. 12 is a flow chart for describing a processing flow of the internal temperature measuring device 10D of the present embodiment.

Communication is established between the mounting instrument 11 and the main body device 1500 (Steps S2 to S4).

When communication is established, the main body device 1500 executes Steps S10 to S16. Meanwhile, the mounting instrument 11 starts measuring the surface temperature and the heat flux with the first sensor module 70A and the second sensor module 70B (Step S32) and starts transmitting measurement data to the main body device 1500 (Step S34). The data may be transmitted through a method in which data is transmitted one by one every time a new measurement value is obtained or a method in which data for a certain period of time is stored in the IC memory 32 and is collectively transmitted.

When the measurement data starts to be received from the mounting instrument 11 (YES in Step S36), the main body device 1500 starts calculating and recording the internal temperature (Step S70), and starts performing processing of displaying the calculated internal temperature (Step S72). A touch panel 1506 (refer to FIG. 11) included in the main body device 1500 may display the internal temperature. Otherwise, data of the calculated internal temperature may be transmitted to the mounting instrument 11, and the mounting instrument 11 may cause the display section 16 to display the data. Naturally, both methods may be adopted.

According to the present embodiment, it is possible to obtain an effect similar to that of the first embodiment. According to the present embodiment, since a burden of computation processing in the mounting instrument 11 can be reduced, the CPU 31 can be realized at low price. Since the storage domain required to store the data of the calculated internal temperature can be reduced, the mounting instrument 11 can be further reduced in size, weight, and manufacturing cost compared to that of the internal temperature measuring device 10 of the first embodiment. The main body device 1500 excels in portability and has a display device greater than the display section 16, thereby having merits in that an analysis result such as a graph of internal temperatures can be displayed so as to be easy to see and to understand, compared to the first embodiment.

MODIFICATION EXAMPLE

Hereinbefore, description has been given regarding the embodiments of the invention are applied. However, the configuration elements can be suitably added, omitted, and changed.

First Modification Example

Figure 13:
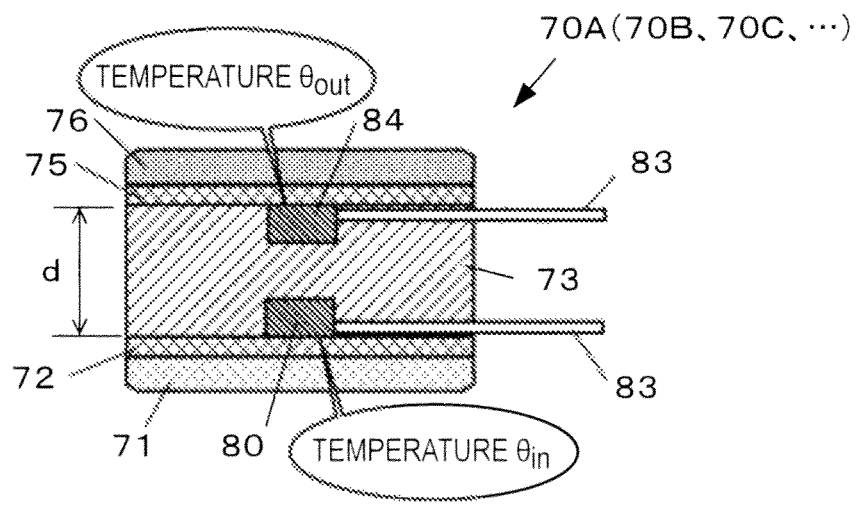
FIG. 13 is a cross-sectional view illustrating a modification example of a configuration of a sensor module.

For example, the sensor module of the above-described embodiments is configured to be equipped with the temperature sensor 80 and the heat flow sensor 82. However, as illustrated in FIG. 13, in place of the heat flow sensor 82, the sensor module may be equipped with a second temperature sensor 84 at a position farther from the measurement target than the temperature sensor 80. A heat flux $\phi_q$ may be configured to be calculated through Expression (19) based on a temperature $\theta_{in}$ (the surface temperature of the measurement target) measured with the temperature sensor 80, and a temperature $\theta_{out}$ measured with the second temperature sensor 84.

$$\phi_q = \frac{\lambda_s}{d}(\theta_{in} - \theta_{out})  \qquad \text{Expression (19)}$$

$\lambda_s$ W/(m×k): heat conductivity of heat transfer layer 73 in sensor module Naturally, in this case as well, the sensor module measures the temperature and the heat flux in the same manner.

Second Modification Example

In the above-described embodiments, a function of calculating base metabolism based on the internal temperature $\theta(0)$ can be added. Specifically, the body temperature of a person is maintained at approximately 37° C. However, generally, the outside air temperature of an environment where people spend time ranges approximately from 20° C. to 28° C., which is lower than the body temperature. Therefore, there is a temperature difference between the body temperature of a person and the environment temperature, and a person radiates heat to the environment at all times. Due to this heat radiation, the human body performs heat production in order to maintain the body temperature. Metabolism corresponding to the heat production carried out in order to maintain the body temperature is called base metabolism. Accordingly, measurement of the base metabolism may be performed through measurement of a heat quantity radiated from a human body to the external environment.

When measuring a heat quantity radiated from a human body to the external environment, the heat quantity radiated from the body surface per unit time and unit surface area, that is, the heat flux is measured, and the results may be integrated by a body surface area BSA as described in Expression (20).

$$Q = \phi_q \cdot BSA \qquad \text{Expression (20)}$$

Q W=J/S: heat flow: heat quantity per unit time
$\phi_q$ W/m$^2$: heat flux
BSA m$^2$: body surface area The heat flux $\phi_q$ can be averagely calculated through Expression (21) based on the first heat flux $\phi_{qa}$ and the second heat flux $\phi_{qb}$ respectively measured with the first sensor module 70A and the second sensor module 70B.

$$\phi_q = \frac{\phi_{qa} + \phi_{qb}}{2} \qquad \text{Expression (21)}$$

Accordingly, in the above-described embodiments, base metabolism Mb can be obtained through Expression (22).

$$Mb = \int Q ds = \int \phi_q \cdot BSA ds = \int \left(\frac{\phi_{qa} + \phi_{qb}}{2}\right) BSA ds \qquad \text{Expression (22)}$$

The heat flux $\phi_q$ may be calculated by adopting predetermined constants $K_a$ and $K_b$ as in Expression (23) and generating a heat conduction model of a wrist in a simulation, based on a relationship between an overall heat flow measurement value around the wrist in the simulation, and the measurement values of the first sensor module 70A and the second sensor module 70B respectively disposed on the back side and the palm side of the wrist.

$$\phi_q = K_a \phi_{qa} + K_b \phi_{qb} \qquad \text{Expression (23)}$$

In the present embodiment, the body surface area BSA is obtained based on a height H cm and a weight Wt kg by adopting the Du Bois equation indicated in Expression (24).

$$BSA = H^{0.725} \times Wt^{0.425} \times 0.007184 \qquad \text{Expression (24)}$$

Figure 14:
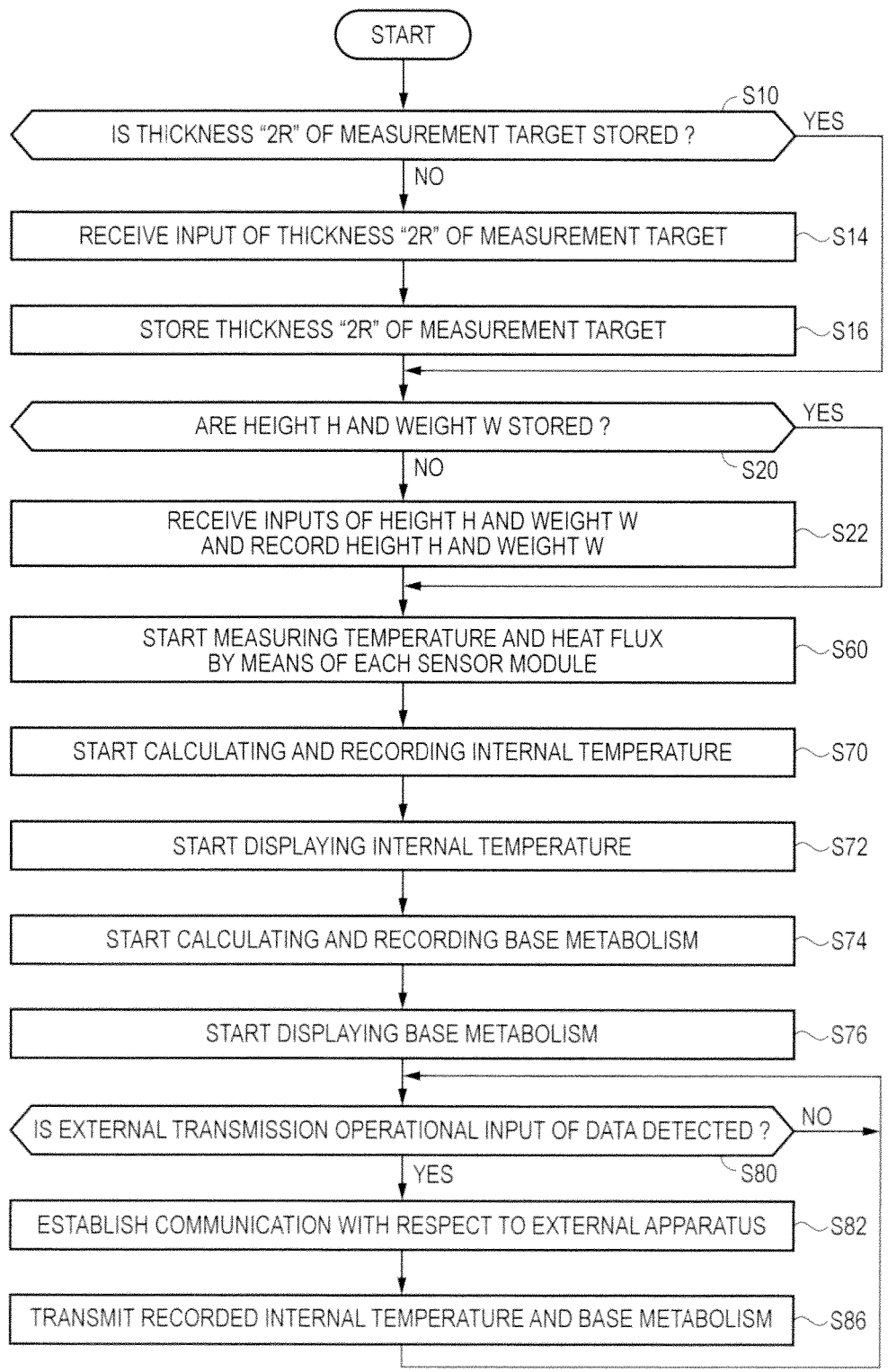
FIG. 14 is a flow chart for describing a processing flow in a case where a function of calculating base metabolism is added to the first embodiment.

FIG. 14 is a flow chart for describing a processing flow in a case where a function of calculating the base metabolism Mb is added to the first embodiment. Basically, the processing flow is similar to that of the first embodiment. However, subsequently to Step S16, when the user's height and weight are not stored in a predetermined storage domain of the IC memory 32 (NO in Step S20), the internal temperature measuring device 10 receives inputs of the height and the weight, and each of the input values is stored (Step S22). When calculation of the internal temperature starts, the internal temperature measuring device 10 starts calculating the body surface area through Expression (24) and calculating the base metabolism Mb through Expression (22) (Step S74), thereby starting processing of causing the display section 16 to display the calculated base metabolism Mb (Step S76).

Third Modification Example

A method of obtaining the function of the internal temperature distribution $\theta(r)$ can be suitably set without being limited to the example of the above-described embodiments. For example, the function of the internal temperature distribution $\theta(r)$ may be obtained by adopting a modified Bessel function.

Specifically, Expression (1) is a differential equation related to the temperature, and the temperature of tissue inside a living body can be obtained by solving the differential equation. More specifically, regarding the variable in Expression (1), the temperature $\theta_{ar}$ of arterial blood is known to be substantially equal to the body temperature (=approximately 37° C.). There is little fluctuation of thermogenesis M caused due to metabolism of tissue. Accordingly, when the two factors are respectively referred to as a constant a and a constant b, the solution of Expression (1) can be expressed through Expression (25) by adopting the modified Bessel function.

$$\theta(r) = C_1 I_0(\sqrt{ar}) + C_2 K_0(\sqrt{ar}) + \frac{b}{a} \qquad \text{Expression (25)}$$

$\theta(r)$° C.: temperature over distance r
$a(=K)W/(m^3 \times K)$: blood-flow heat proportionality constant
$b(=M+K\theta_{ar})W/m^3$: thermogenesis constant
$I_0$: 0th order first-type modified Bessel function
$K_0$: 0th order second-type modified Bessel function
$C_1$, $C_2$: unknown constants
Since Expression (25) is the function of the internal temperature distribution, when the function thereof is differentiated by the distance r and the heat conductivity $\lambda$ of tissue is integrated, the heat flux is obtained, and the heat flux can be expressed through Expression (26).

$$\phi_q(r) = \lambda \frac{\partial}{\partial r} \theta(r) = \lambda \{ C_1 \sqrt{a} \, I_1(\sqrt{ar}) - C_2 \sqrt{a} \, K_1(\sqrt{ar}) \} \qquad \text{Expression (26)}$$

$\phi q(r) W/m_2$: heat flux over distance r
$\theta(r)$° C.: temperature over distance r
$\lambda$ W/(m×K): heat conductivity of tissue
$I_1$: first order first-type modified Bessel function
$K_1$: first order second-type modified Bessel function
Expression (25) indicates a temperature distribution of a living body, and Expression (26) indicates a heat flux distribution of a living body respectively. When the distance of the highest temperature point $P_0$ in the internal temperature distribution is set to "0", and the distance from the highest temperature point $P_0$ to the surface are respectively referred to as $R_1$ and $R_2$, the temperatures and the heat fluxes at positions of $R_1$ and $R_2$ are the temperatures and the heat fluxes of the surface of a living body, and the temperatures and the heat fluxes can be respectively measured with the first sensor module 70A and the second sensor module 70B of the internal temperature measuring device 10. When the internal temperature measuring device 10 is mounted on the wrist 2 so as to perform measurement, heat resistance of the measurement target contact portion 71 and the external environment contact portion 76 is small enough to be ignored, and thus, four Expressions (27) to (30) are established.

$$\theta_a(r) = C_1 I_0(\sqrt{aR_1}) + C_2 K_0(\sqrt{aR_1}) + \frac{b}{a} \qquad \text{Expression (27)}$$

$$\theta_b(r) = C_1 I_0(\sqrt{aR_2}) + C_2 K_0(\sqrt{aR_2}) + \frac{b}{a} \qquad \text{Expression (28)}$$

$$\phi_{q_a}(r) = \lambda \{ C_1 \sqrt{a} \, I_1(\sqrt{aR_1}) - C_2 \sqrt{a} \, K_1(\sqrt{aR_1}) \} \qquad \text{Expression (29)}$$

$$\phi_{q_b}(r) = \lambda \{ C_1 \sqrt{a} \, I_1(\sqrt{aR_2}) - C_2 \sqrt{a} \, K_1(\sqrt{aR_2}) \} \qquad \text{Expression (30)}$$

When the simultaneous equations of Expressions (27) to (30) are solved, four unknown constants $C_1$, $C_2$, $R_1$, and $R_2$ can be obtained. In this case, the solutions of the simultaneous equations are obtained through numerical analyses under the boundary conditions of $R_1 + R_2 = 2R$. Specifically, the factors $C_1$, $C_2$, $R_1$, and $R_2$ are set to variables, and the solutions are obtained by performing numerical calculation (for example, repeated calculation adopting a least squares method) with a computer such that Expressions (27) to (30) are established. When the obtained factors $C_1$ and $C_2$ are substituted in Expression (25), the temperature distribution inside a living body can be obtained. Accordingly, when r=0 in Expression (25), the internal temperature of a living body at the highest temperature point $P_0$ in the internal temperature distribution, that is, the internal temperature $\theta(0)$ can be obtained.

The blood-flow heat proportionality constant $a(=K)W/(m^3 \times K)$ in Expression (25) may be calculated based on a known correlationship from the first surface temperature $\theta_a$ or the second surface temperature $\theta_b$.

In other words, as it is known that the blood-flow heat proportionality constant $a(=K)$ can be expressed by the product of the blood density $\rho_b$, the specific heat $C_b$ at constant pressure, and the blood flow rate $w_b$ per unit volume, the blood-flow heat proportionality constant $a(=K)$ is proportional to the blood flow rate. Since it is known that the blood flow rate $w_b$ per unit volume of skin and skin temperature are under a correlationship, the blood flow rate $w_b$ per unit volume of skin can be computed based on the correspondence table which is illustrated in FIG. 15 and is measured in advance, by measuring the skin temperature. The blood flow rate $w_b$ per unit volume obtained based on the correspondence table is adopted such that the blood-flow heat proportionality constant a $W/(m^3 \times K) = \rho_b \times C_b \times w_b$ can be obtained.

Fourth Modification Example

A method of obtaining the function of the internal temperature distribution (r) can be suitably set without being limited to the example of the above-described embodiments. For example, the function of the internal temperature distribution θ(r) may be obtained by approximating the function thereof to a multinomial equation related to a distance from the cylinder axis of the cylindrical coordinate system.

Specifically, a particular heat model of a living body on the assumption of the measurement target is generated in a simulation, and the temperature distribution θ(r) of a living body is estimated through a solution method adopting the above-described modified Bessel function. The temperature distribution θ(r) is postulated as a multinomial equation such as Expression (31) having the distribution θ(R) on the surface of the living body as a parameter, and proportionality constants $\alpha_0$ to $\alpha_n$ are obtained for each of the surface temperatures through the least squares method or the like. In other words, sets of the proportionality constants $\alpha_0$ to $\alpha_n$ which are separately obtained for various types of the assumed temperatures θ(R) are stored in the IC memory 32 in advance so as to match the temperatures θ(R).

$$\theta(r) = \theta(R) + \alpha_1(R-r) + \alpha_2(R^2 - r^2) + \ldots + \alpha_n(R^n - r^n) \quad \text{Expression (31)}$$

The first surface temperature $\theta_a$ measured with the first sensor module 70A of the internal temperature measuring device 10 or the second surface temperature $\theta_b$ measured with the second sensor module 70B is substituted for θ(R) in Expression (31), and the sets of the proportionality constants $\alpha_0$ to $\alpha_n$ matching the substituted first surface temperature $\theta_a$ or the substituted second surface temperature $\theta_b$ are read out from the IC memory 32, thereby determining the internal temperature distribution. The highest temperature is calculated based on the determined internal temperature distribution, and the result thereof can be considered to be the internal temperature.

Fifth Modification Example

Figure 16:
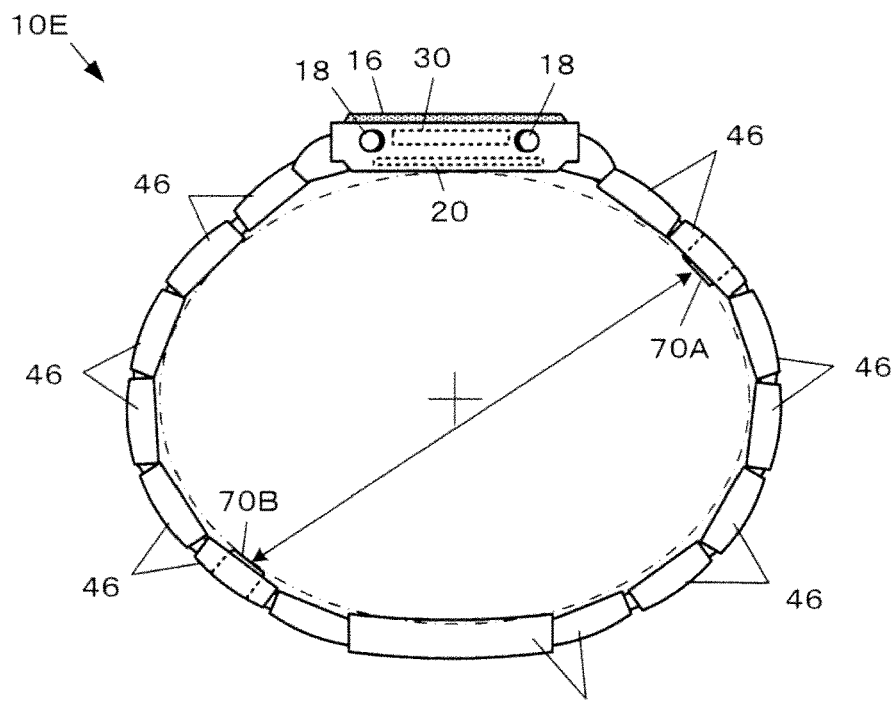
FIG. 16 is a front view illustrating a configuration of an internal temperature measuring device of a fifth modification example.

In the above-described embodiments, the portion mounted on the measurement target is configured to include one measurement unit 12 and one flexible portion 14 or is configured to include two of the back side measuring unit 12U and the palm side measuring unit 12D, two flexible portions 14. However, the embodiments are not limited to the configurations. For example, as in an internal temperature measuring device 10E illustrated in FIG. 16, winding portions (portions corresponding to the measurement unit 12 and the flexible portion 14 of the first embodiment) may be realized by interlocking a plurality of links 46 with each other, such as pieces of a metal band of a wristwatch. In this case, the first sensor module 70A and the second sensor module 70B can be configured to be respectively provided in the links 46 at positions substantially facing other, among the plurality of links 46.

Sixth Modification Example

Figure 17:
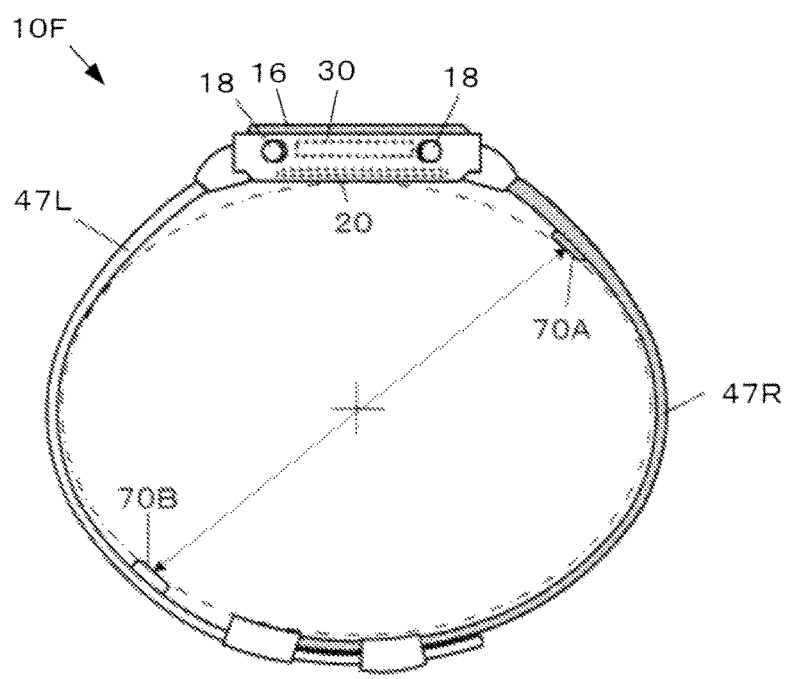
FIG. 17 is a front view illustrating a configuration of an internal temperature measuring device of a sixth modification example.

Moreover, when the portion mounted on the measurement target has a configuration in which a user can adjust the length thereof in person, the flexible portion 14 can be omitted. For example, as in an internal temperature measuring device 10F illustrated in FIG. 17, the first sensor module 70A and the second sensor module 70B can be configured to be respectively provided in elastomeric resin belts 47R and 47L of which the belt lengths can be minutely adjusted.

Seventh Modification Example

In the above-described embodiments, the sensor module used in measurement is determined in advance. However, a pair of sensor modules suitable for the measurement can be configured to be selected from a number of sensor modules.

Figure 18:
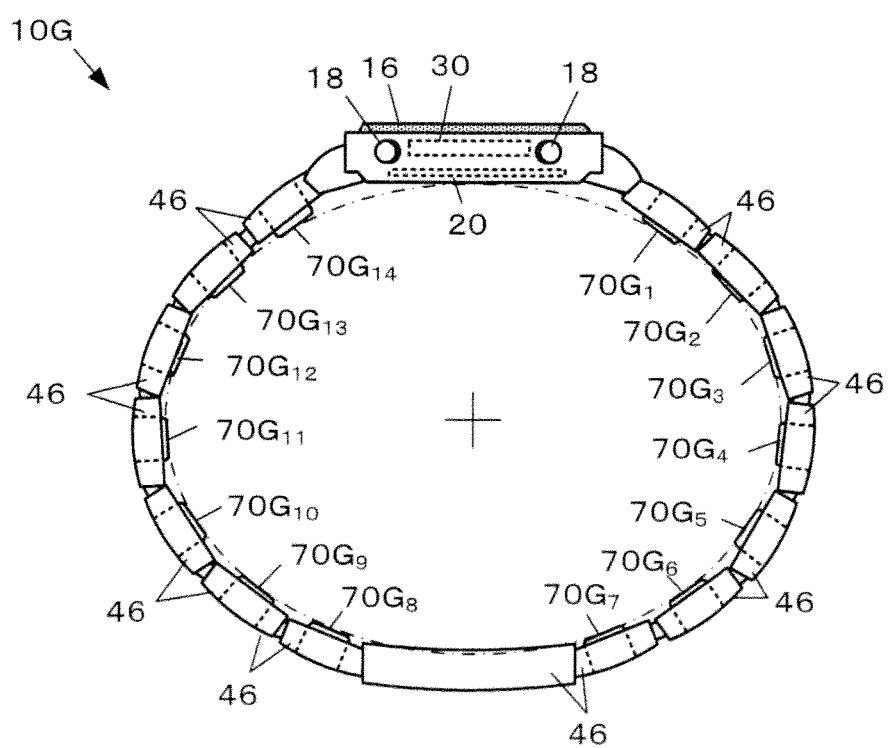
FIG. 18 is a front view illustrating a configuration of an internal temperature measuring device of a seventh modification example.

For example, as illustrated in FIG. 18, a plurality, that is, three or more sensor modules $70G_1$, $70G_2$, and so forth are circumferentially disposed in an internal temperature measuring device 10G so as to surround the internal position of the surface of the measurement target. In the example in FIG. 18, since a watch-type internal temperature measuring device is assumed, winding portions are realized by interlocking the plurality of links 46 with each other, such as pieces of a metal band of a wristwatch, and the links 46 are respectively equipped with the sensor modules $70G_1$, $70G_2$, and so forth up to $70G_{14}$. Naturally, the number of sensor modules to be equipped with can be suitably set without being limited to the illustrated example. When the first embodiment or the second embodiment is applied as the base, each of the back side measuring unit 12U and the palm side measuring unit 12D may be equipped with a plurality of sensor modules.

Figure 19:
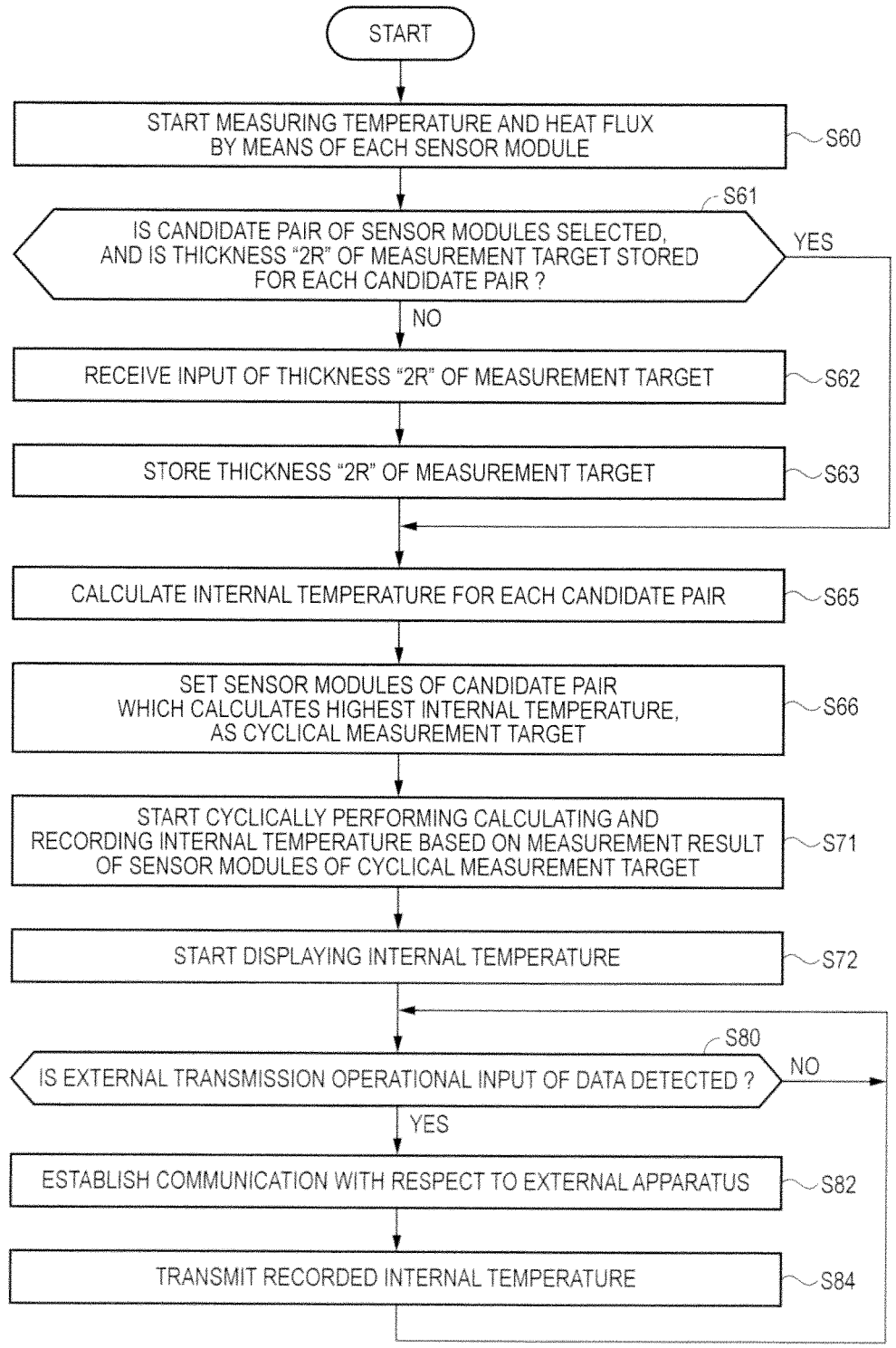
FIG. 19 is a flow chart for describing a processing flow of the internal temperature measuring device of the seventh modification example.

When the first embodiment is applied as the base, as illustrated in FIG. 19, the internal temperature measuring device 10G selects a pair appropriate for measurement from the pairs of sensor modules and cyclically executes measurement with the selected pair of sensor modules.

In other words, a procedure is executed as described below. Subsequently to Step S60, the internal temperature measuring device 10G selects a candidate pair of sensors from the sensor modules $70G_1$, $70G_2$, and so forth up to $70G_{14}$ and checks whether or not the thickness "2R" of the measurement target is recorded for each of the selected candidate pairs of sensors (Step S61). If the thickness "2R" thereof is not stored (NO in Step S61), the processing of receiving an input of the thickness "2R" of the measurement target is executed (Step S62), and the input value is stored as the thickness "2R" of the measurement target (Step S63). Next, the internal temperature is calculated for each candidate pair of sensors (Step S67). However, in the selected candidate pairs, the pair of sensors which are disposed at positions adjacent to each other may be omitted.

Subsequently, the internal temperature measuring device 10G sets the sensor module having the candidate pair of sensors indicating the highest temperature among the calculated internal temperatures for each candidate pair of sensors, as the sensor which is used in the cyclical measurement (Step S66). In place of Step S70, calculating and recording of the internal temperature start to be cyclically performed based on the measurement result of the sensor module which is set as the cyclical measurement target (Step S71).

Figure 20:
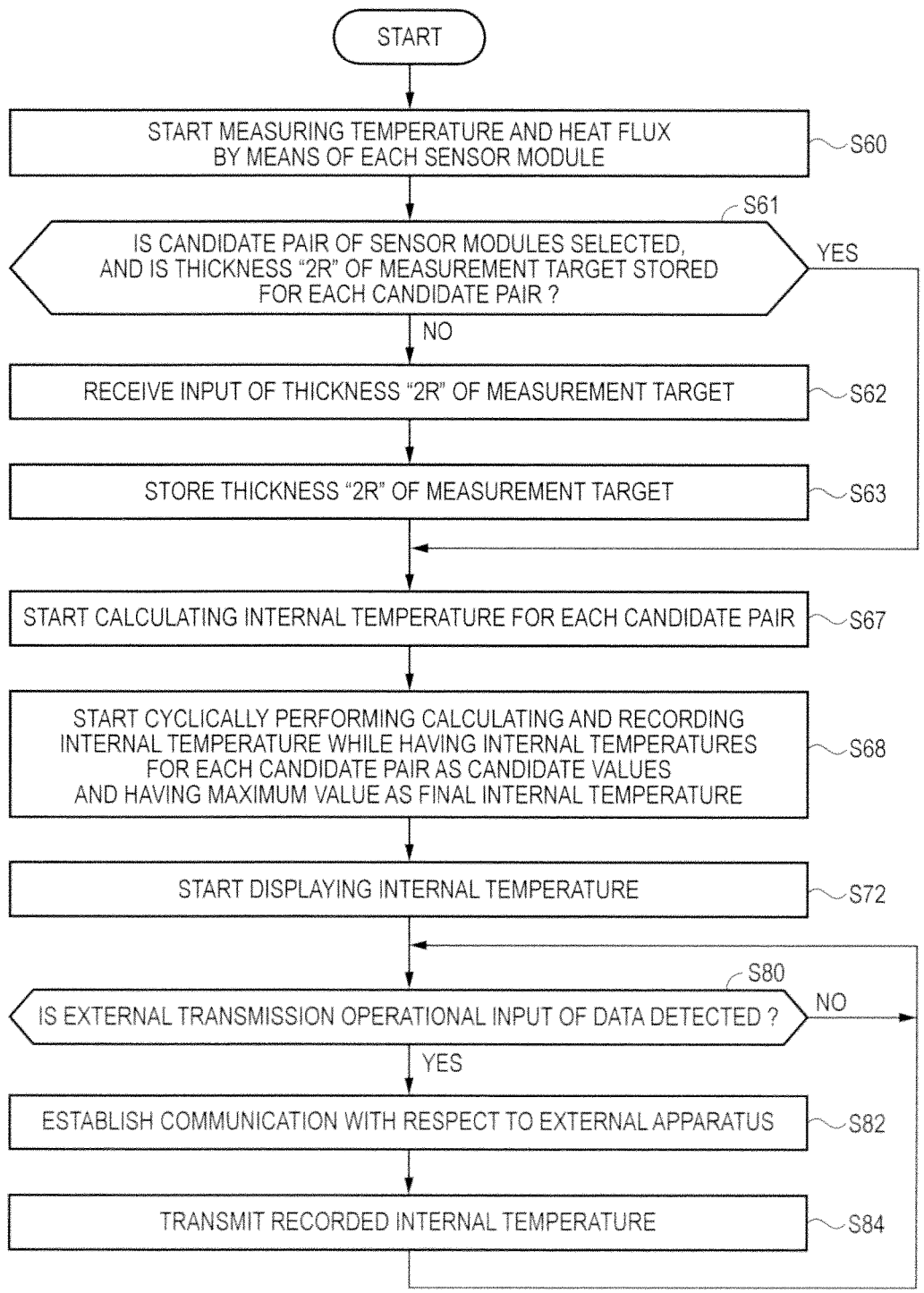
FIG. 20 is a flow chart for describing another processing flow of the internal temperature measuring device of the seventh modification example.

Otherwise, the flow chart for describing the processing flow illustrated in FIG. 20 may be adopted.

In other words, a procedure is executed as described below. Subsequently to Step S60, the internal temperature measuring device 10G selects a candidate pair of sensors from the sensor modules $70G_1$, $70G_2$, and so forth up to $70G_{14}$ and checks whether or not the thickness "2R" of the measurement target is recorded for each of the selected candidate pairs of sensors (Step S61). If the thickness "2R" thereof is not stored (NO in Step S61), the processing of receiving an input of the thickness "2R" of the measurement target is executed (Step S62), and the input value is stored as the thickness "2R" of the measurement target (Step S63). Next, the internal temperature starts to be calculated for each candidate pair of sensors (Step S67). Subsequently, while having the internal temperatures for each candidate pair of sensors as candidate values, processing of recording the candidate value satisfying predetermined conditions (in the configuration thereof, a maximum value) as the final internal temperature from the candidate values starts (Step S68).

According to the configuration of the modification example, the internal temperature can be more accurately measured.

What is claimed is:

1. An internal temperature measuring device comprising:
   an acquisition unit that acquires a one side temperature and a one side heat flux of a measurement target on a one side surface side and an opposite side temperature and an opposite side heat flux of the measurement target on an opposite side surface side; and
   a processor that acts as a computation unit that computes an internal temperature of the measurement target by applying the one side temperature, the one side heat flux, the opposite side temperature, and the opposite side heat flux.

2. The internal temperature measuring device according to claim 1, further comprising:
   a measurement unit that includes N (N≥3) sensor sections which are circumferentially disposed so as to surround the surface of the measurement target and measure a temperature and a heat flux,
   wherein the acquisition unit selects a plurality of pairs of sensor sections in each pair of which a sensor section on the one side surface side and a sensor section on the opposite side surface side are combined together from the N sensor sections, and acquires a measurement result by means of each of the pairs of sensor sections, and
   wherein the processor acting as the computation unit estimates a candidate of the internal temperature for each pair of sensor sections by applying the measurement result of the pair of sensor sections obtained by means of the acquisition unit, and causes a candidate satisfying a predetermined condition to be determined as a final internal temperature from the candidates.

3. A wrist mounting-type device in which a measurement target is a wrist of a human body and which has an annular shape and is mounted on the wrist, the device comprising:
   the internal temperature measuring device according to claim 2.

4. The internal temperature measuring device according to claim 1, further comprising:
   a sensor section that measures a temperature and a heat flux and is changeably disposed between the one side surface side and the opposite side surface side,
   wherein the acquisition unit acquires a measurement result obtained when the sensor section is disposed on the one side surface side as the one side temperature and the one side heat flux, and acquires a measurement result obtained when the sensor section is disposed on the opposite side surface side as the opposite side temperature and the opposite side heat flux.

5. A wrist mounting-type device in which a measurement target is a wrist of a human body and which has an annular shape and is mounted on the wrist, the device comprising:
   the internal temperature measuring device according to claim 4.

6. The internal temperature measuring device according to claim 1,
   wherein the processor acting as the computation unit computes the internal temperature of the measurement target by applying a predetermined temperature distribution indicating temperatures inside the measurement target.

7. A wrist mounting-type device in which a measurement target is a wrist of a human body and which has an annular shape and is mounted on the wrist, the device comprising:
   the internal temperature measuring device according to claim 6.

8. The internal temperature measuring device according to claim 1,
   wherein the temperature distribution is expressed through an Nth order function (N≥2) in which the internal temperature of the measurement target is a temperature peak.

9. A wrist mounting-type device in which a measurement target is a wrist of a human body and which has an annular shape and is mounted on the wrist, the device comprising:
   the internal temperature measuring device according to claim 8.

10. The internal temperature measuring device according to claim 1,
    wherein the measurement target is four limbs of a human body, and
    wherein the processor acting as the computation unit also computes base metabolism by applying the one side heat flux and the opposite side heat flux.

11. A wrist mounting-type device in which a measurement target is a wrist of a human body and which has an annular shape and is mounted on the wrist, the device comprising:
    the internal temperature measuring device according to claim 10.

12. A wrist mounting-type device in which a measurement target is a wrist of a human body and which has an annular shape and is mounted on the wrist, the device comprising:
    the internal temperature measuring device according to claim 1.

13. The internal temperature measuring device according to claim 1, further comprising:
    a measurement unit that includes a one side sensor section which measures the one side temperature and the one side heat flux and is provided on the one side surface side of the measurement target, and an opposite side sensor section which measures the opposite side temperature and the opposite side heat flux and is provided on the opposite side surface side of the measurement target,
    wherein the acquisition unit acquires a measurement result by means of the one side sensor section and the opposite side sensor section.

14. The internal temperature measuring device according to claim 13,
    wherein the measurement target is four limbs of a human body, wherein the measurement unit is internally housed in each of annular mounting instruments which are mounted on the four limbs,
wherein the acquisition unit and the computation unit are internally housed in a main body device, and
wherein each of the mounting instruments and the main body device are configured to be connected so as to perform communication therebetween.

15. A wrist mounting-type device in which a measurement target is a wrist of a human body and which has an annular shape and is mounted on the wrist, the device comprising:
the internal temperature measuring device according to claim 13.

16. The internal temperature measuring device according to claim 13,
wherein the one side sensor section includes a plurality of temperature sensors,
wherein the opposite side sensor section includes a plurality of temperature sensors, and
wherein the acquisition unit acquires a one side heat flow from a plurality of temperatures measured with the one side sensor section and acquires an opposite side heat flow from a plurality of temperatures measured with the opposite side sensor section.

17. A wrist mounting-type device in which a measurement target is a wrist of a human body and which has an annular shape and is mounted on the wrist, the device comprising:
the internal temperature measuring device according to claim 16.

18. The internal temperature measuring device according to claim 13,
wherein the measurement unit includes a first pair of sensor sections which are provided so as to interpose a first internal position of the measurement target, and a second pair of sensor sections which are provided so as to interpose a second internal position of the measurement target, and
wherein the processor acting as the computation unit estimates a first internal temperature by applying a measurement result obtained by means of the first pair of sensor sections, estimates a second internal temperature by applying a measurement result obtained by means of the second pair of sensor sections, and determines a final internal temperature by applying the first internal temperature and the second internal temperature.

19. A wrist mounting-type device in which a measurement target is a wrist of a human body and which has an annular shape and is mounted on the wrist, the device comprising:
the internal temperature measuring device according to claim 18.

20. A method of measuring an internal temperature of a measurement target through computation processing executed by a computer, the method comprising:
acquiring a one side temperature and a one side heat flux of the measurement target on a one side surface side, and an opposite side temperature and an opposite side heat flux of the measurement target on an opposite side surface side; and
computing the internal temperature of the measurement target by applying the one side temperature, the one side heat flux, the opposite side temperature, and the opposite side heat flux.

21. An internal temperature measuring device comprising:
opposing sensors configured to be placed on and only come into contact with opposite external sides of a portion of a subject to acquire temperature and heat fluxes; and
a processor that acts as a computation unit that computes an internal temperature of the portion of the subject using the acquired temperature and heat fluxes, and without the use of a heater.

22. The internal temperature measuring device according to claim 21,
wherein the opposing sensors comprise a first sensor having a first measurement target contact portion configured to come into contact with and be placed only on a first side surface side of the portion of a subject to acquire a first temperature and a first heat flux, and a second sensor having a second measurement target contact portion configured to come into contact with and be placed only on a second side surface side of the portion of the subject to acquire a second temperature and a second heat flux, the first side surface side being opposite to the second side surface side; and
the processor acting as the computation unit computes the internal temperature of the measurement target by applying the first side temperature, the first side heat flux, the second side temperature, and the second side heat flux, without the use of the heater.

23. The internal temperature measuring device according to claim 21, wherein the opposing sensors comprise a first sensor and a second sensor, wherein the first sensor is configured to be positioned farther from a measurement target than the second sensor.

24. The internal temperature measuring device according to claim 21, wherein the portion of a subject is a skin surface of a wrist of the subject, and further comprising:
a measurement unit including the opposing sensors, the measurement unit having an arc shape in a frontal view, and a flexible portion connecting end portions of the measurement unit to each other, the measurement unit being an integral molding article formed from an elastomeric resin having a C shape in a frontal view, the measurement unit being warped due to a force caused by the flexible portion tending to contract, and each of a back side inner surface and a palm side inner surface of the measurement unit configured to be in tight contact with the skin surface of the wrist.

25. The internal temperature measuring device according to claim 24,
wherein measurement unit is configured to be positioned with the opposing sensors in a vicinity of a substantial center in a direction connecting a back side and a palm side of the wrist with respect to an ulnar artery and a radial artery on the palm side of an ulna and a radius in the wrist.

* * * * *